(12) United States Patent
Sampson et al.

(10) Patent No.: US 7,405,283 B2
(45) Date of Patent: Jul. 29, 2008

(54) SCREENING METHODS AND SEQUENCES RELATING THERETO

(75) Inventors: Julian R. Sampson, Llandaff (GB); Jeremy Peter Cheadle, Bichgrove (GB)

(73) Assignee: University of Wales, Cardiff (GB)

( * ) Notice: Subject to any disclaimer, the term of this patent is extended or adjusted under 35 U.S.C. 154(b) by 0 days.

(21) Appl. No.: 10/485,999

(22) PCT Filed: Aug. 2, 2002

(86) PCT No.: PCT/GB02/03591

§ 371 (c)(1),
(2), (4) Date: Jul. 14, 2004

(87) PCT Pub. No.: WO03/014390

PCT Pub. Date: Feb. 20, 2003

(65) Prior Publication Data

US 2005/0003359 A1 Jan. 6, 2005

(30) Foreign Application Priority Data

Aug. 3, 2001 (GB) .................................. 0118995.0

(51) Int. Cl.
*C07H 21/02* (2006.01)
(52) U.S. Cl. .................................................. 536/23.1
(58) Field of Classification Search ................. 536/23.1
See application file for complete search history.

(56) References Cited

U.S. PATENT DOCUMENTS

| 6,013,473 | A |   | 1/2000  | Wei         |          |
|-----------|---|---|---------|-------------|----------|
| 6,051,222 | A |   | 4/2000  | Wei         |          |
| 6,060,594 | A | * | 5/2000  | English et al. | 536/23.71 |
| 6,639,063 | B1| * | 10/2003 | Edwards et al. | 536/23.5  |

FOREIGN PATENT DOCUMENTS

WO      WO 97/33903       9/1997

OTHER PUBLICATIONS

1997/1998 Stratagene catalog (p. 118, 1997/1998).*
Jones et al., "Biallelic germline mutations in MYH predispose to multiple colorectal adenoma and somatic G:C→T: A mutations", *Human Molecular Genetics*, Nov. 1, 2002, 11(23):2961-2967.
Shinmura et al. Somatic Mutations and Single Nucleotide polymorphins . . . Cancer Letters 166. Jan. 2001. pp. 65-69.
Gu et al. Differential DNA Recognition and Glycosylase activity of the native human . . . Nucleic Acids Research. 2001. vol. 29, No. 12. pp. 2666-2674.
Tsuzuki et al. Analysis of MTH1 gene function in mice with targeted mutagenesis. Mutation Research 477. 2001. pp. 71-78.
Ohtsubo et al. Identification of Human MutY Homolog (hMYH) as a repair enzyme . . . Nucleic Acids Research, 2000, vol. 28, No. 6 pp. 1355-1364.
Nakabeppu. Molecular genetics and structural biology of human MutT homolog, MTH1. Mutation Research 477. 2001. pp. 59-70.
H. Wikman et al. hOGG1 Polymorphism and Loss of Heterozygosity (LOH): Significance for Lung Cancer . . . Int. J. Cancer, 88, 2000, pp. 932-937.
Sugimura et al. hOGG1 ser326Cys Polymorphism and Lung cancer Susceptibility. Cancer Epidemiology, Biomarkers and Prevention. 1999. vol. 8, pp. 669-674.
Al-Tassan et al. Inherited variants of MYH associated with somatic G:C→T:A mutations in. Nature Genetics, vol. 30, 2002. pp. 227-232.
Audebert et al. Effect of single mutations in OGG1 gene found in human tumors . . . Nucleic Acids Research, 2000, vol. 28, No. 14, pp. 2672-2678.
Shinmura et al. Infrequent mutations of the hOGG1 gene, that is involved in the excision . . . Jpn J. Cancer Research. 1998, vol. 89, pp. 825-828.
Boiteux et al. The Human OGG1 Gene: Structure, Functions, and its Implication . . . Archives of Biochemistry and Biophysics. vol. 377, No. 1, 2000, pp. 1-8.
Fearnhead et al. The ABC of APC. Human Molecular Genetics, 2001. vol. 10, No. 7. pp. 721-733.
Slupska et al. Cloning and Sequencing a Human homolog (hMYH) of the *Escherichia coli* mutY gene whose function is required for the repair of oxidative DNA damage. Journal of Bacteriology, Jul. 1996, pp. 3885-3892.

* cited by examiner

*Primary Examiner*—Misook Yu
*Assistant Examiner*—Sean E Aeder
(74) *Attorney, Agent, or Firm*—Andrew Gibbs; Jay Z. Zhang; Myriad IP Department

(57) ABSTRACT

A screening method for identifying an individual having a pre-disposition towards having a cancer is disclosed, which screening method comprises the steps of: (a) obtaining a test sample comprising a nucleotide sequence comprised in a gene in a gene in a base excision repair (BER) pathway of the individual or an amino acid sequence of a polypeptide expressed thereby; and (b) comparing a region of the test sample sequence with the corresponding region of the wild type sequence, whereby a difference between the test sample sequence and the wild type sequence signifies that the individual is pre-disposed to having the cancer; and wherein the difference comprises a specified variation. The specified variation can be the known mutation in the human MYH protein, G382D-hMYH or a nucleotide sequence encoding it, or it can be one or more novel variations, namely, Y165C, E466X, and Y90X, or the respective corresponding nucleotide sequences. The method is particularly suitable for determining a pre-disposition towards bowel cancer.

9 Claims, 8 Drawing Sheets

Figure 1:
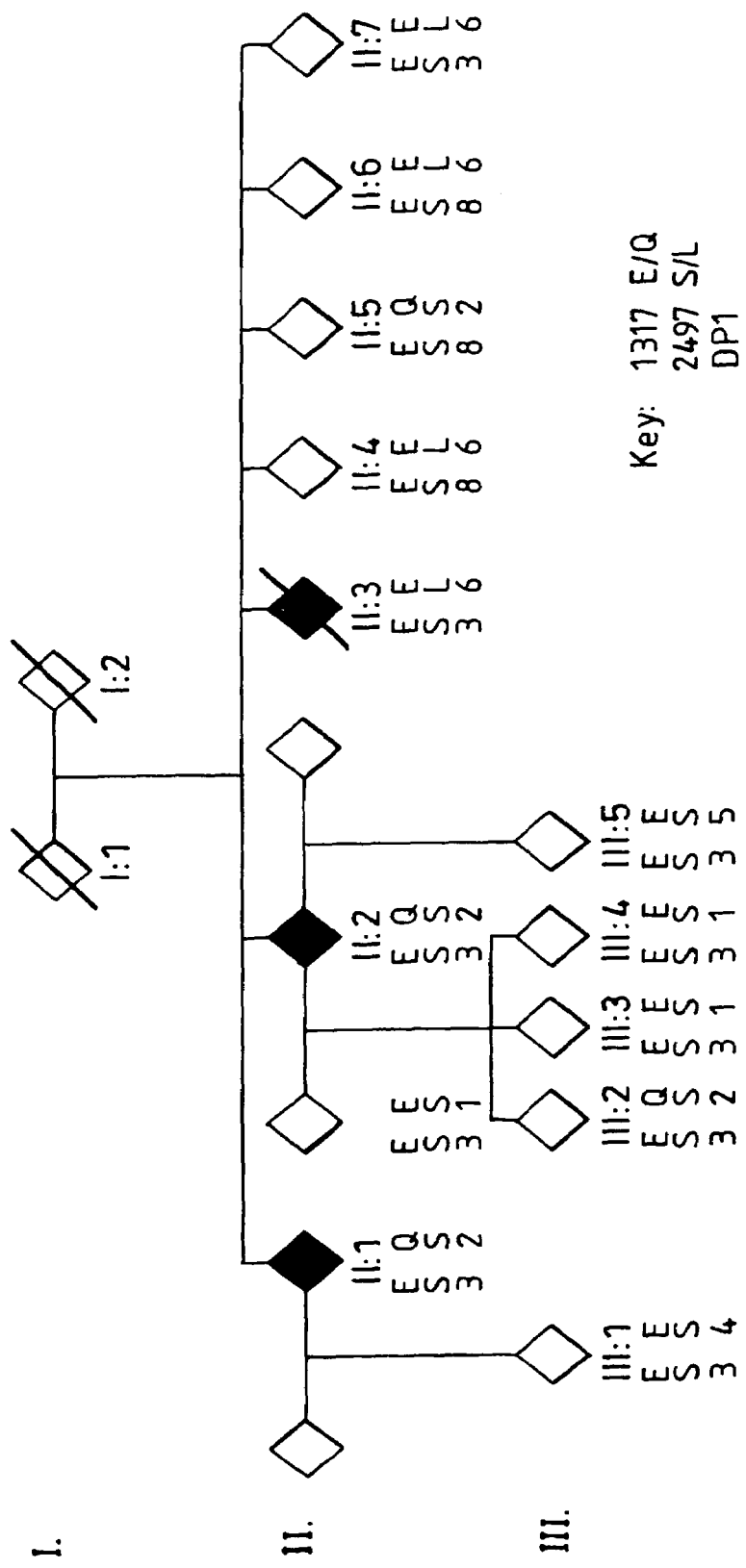

Fig. 4(a)
Fig. 4(b)

SEQUENCE LISTING

<160> NUMBER OF SEQ IDS NOS: 133

<210> SEQ ID NO 1
<211> LENGTH: 23
<212> TYPE: DNA
<213> ORGANISM: Homo sapiens

<400> SEQUENCE: 1
tgcagtcttt attagcattg ttt                                          23

<210> SEQ ID NO 2
<211> LENGTH: 23
<212> TYPE: DNA
<213> ORGANISM: Homo sapiens

<400> SEQUENCE: 2
ttcaaataag ttgtactgcc aag                                          23

<210> SEQ ID NO 3
<211> LENGTH: 25
<212> TYPE: DNA
<213> ORGANISM: Homo sapiens

<400> SEQUENCE: 3
gcaaatccta agagagaaca actgt                                        25

<210> SEQ ID NO 4
<211> LENGTH: 25
<212> TYPE: DNA
<213> ORGANISM: Homo sapiens

<400> SEQUENCE: 4
tccagaacaa aaccctcta acaag                                         25

<210> SEQ ID NO 5
<211> LENGTH: 20
<212> TYPE: DNA
<213> ORGANISM: Homo sapiens

<400> SEQUENCE: 5
ccttcaatag gcgtgtaatg                                              20

<210> SEQ ID NO 6
<211> LENGTH: 20
<212> TYPE: DNA
<213> ORGANISM: Homo sapiens

<400> SEQUENCE: 6
aaagcagtaa aaccgaacat                                              20

<210> SEQ ID NO 7
<211> LENGTH: 23
<212> TYPE: DNA
<213> ORGANISM: Homo sapiens

<400> SEQUENCE: 7
tcaaatatgg cttccagaac aaa                                          23

<210> SEQ ID NO 8
<211> LENGTH: 25
<212> TYPE: DNA
<213> ORGANISM: Homo sapiens

<400> SEQUENCE: 8
gctgatccca gcagcaccct tgttt                                        25

<210> SEQ ID NO 9
<211> LENGTH: 25
<212> TYPE: DNA
<213> ORGANISM: Homo sapiens

<400> SEQUENCE: 9 aatggggct ttcagaggtg tcact                                         25

<210> SEQ ID NO 10
<211> LENGTH: 22
<212> TYPE: DNA
<213> ORGANISM: Homo sapiens

<400> SEQUENCE: 10
gagggtttgt aaatggaagc ag                                           22

<210> SEQ ID NO 11
<211> LENGTH: 22
<212> TYPE: DNA
<213> ORGANISM: Homo sapiens

<400> SEQUENCE: 11
ctcatgcagc ctttcataga gc                                           22

<210> SEQ ID NO 12
<211> LENGTH: 20
<212> TYPE: DNA
<213> ORGANISM: Homo sapiens

<400> SEQUENCE: 12
gtggtcaact tccccagaaa                                              20

<210> SEQ ID NO 13
<211> LENGTH: 20
<212> TYPE: DNA
<213> ORGANISM: Homo sapiens

<400> SEQUENCE: 13
ggccagccca tatacttgat                                              20

<210> SEQ ID NO 14
<211> LENGTH: 20
<212> TYPE: DNA
<213> ORGANISM: Homo sapiens

<400> SEQUENCE: 14
atggctgcag cttcatatga                                              20

<210> SEQ ID NO 15
<211> LENGTH: 19
<212> TYPE: DNA
<213> ORGANISM: Homo sapiens

<400> SEQUENCE: 15
gctgtcttgg gagctagac                                               19

<210> SEQ ID NO 16
<211> LENGTH: 19
<212> TYPE: DNA

<213> ORGANISM: Homo sapiens

<400> SEQUENCE: 16
accatgaaac agccagtgt					19

<210> SEQ ID NO 17
<211> LENGTH: 19
<212> TYPE: DNA
<213> ORGANISM: Homo sapiens

<400> SEQUENCE: 17
ctgtggtcct catttgtag					19

<210> SEQ ID NO 18
<211> LENGTH: 20
<212> TYPE: DNA
<213> ORGANISM: Homo sapiens

<400> SEQUENCE: 18
gcaaatccta agagagaaca					20

<210> SEQ ID NO 19
<211> LENGTH: 20
<212> TYPE: DNA
<213> ORGANISM: Homo sapiens

<400> SEQUENCE: 19
gactttgcct tccagagttc					20

<210> SEQ ID NO 20
<211> LENGTH: 21
<212> TYPE: DNA
<213> ORGANISM: Homo sapiens

<400> SEQUENCE: 20
aagctctgct gcccatacac a					21

<210> SEQ ID NO 21
<211> LENGTH: 20
<212> TYPE: DNA
<213> ORGANISM: Homo sapiens

<400> SEQUENCE: 21
ctgctatttg cagggtatta					20

<210> SEQ ID NO 22
<211> LENGTH: 20
<212> TYPE: DNA
<213> ORGANISM: Homo sapiens

<400> SEQUENCE: 22
aaagcagtaa aaccgaacat					20

<210> SEQ ID NO 23
<211> LENGTH: 20
<212> TYPE: DNA
<213> ORGANISM: Homo sapiens

<400> SEQUENCE: 23
ttgttggcat ggcagaaata					20

<210> SEQ ID NO 24
<211> LENGTH: 20

<212> TYPE: DNA
<213> ORGANISM: Homo sapiens

<400> SEQUENCE: 24
ttcttccaga tgctgatact                                           20

<210> SEQ ID NO 25
<211> LENGTH: 20
<212> TYPE: DNA
<213> ORGANISM: Homo sapiens

<400> SEQUENCE: 25
ccttcaatag gcgtgtaatg                                           20

<210> SEQ ID NO 26
<211> LENGTH: 20
<212> TYPE: DNA
<213> ORGANISM: Homo sapiens

<400> SEQUENCE: 26
gcccaaaggg aaaagtcaca                                           20

<210> SEQ ID NO 27
<211> LENGTH: 20
<212> TYPE: DNA
<213> ORGANISM: Homo sapiens

<400> SEQUENCE: 27
atttgcacct tcctgaatag                                           20

<210> SEQ ID NO 28
<211> LENGTH: 19
<212> TYPE: DNA
<213> ORGANISM: Homo sapiens

<400> SEQUENCE: 28
cctgactcac agggagaac                                            19

<210> SEQ ID NO 29
<211> LENGTH: 20
<212> TYPE: DNA
<213> ORGANISM: Homo sapiens

<400> SEQUENCE: 29
ctgtctacct ggagatgtat                                           20

<210> SEQ ID NO 30
<211> LENGTH: 20
<212> TYPE: DNA
<213> ORGANISM: Homo sapiens

<400> SEQUENCE: 30
gcctccaaaa gccctagtga                                           20

<210> SEQ ID NO 31
<211> LENGTH: 21
<212> TYPE: DNA
<213> ORGANISM: Homo sapiens

<400> SEQUENCE: 31
agcacctgag gaaacggtct g                                         21

<210> SEQ ID NO 32

-continued

```
<211> LENGTH: 20
<212> TYPE: DNA
<213> ORGANISM: Homo sapiens

<400> SEQUENCE: 32
gaaaactccc acctaatctc                                                    20

<210> SEQ ID NO 33
<211> LENGTH: 20
<212> TYPE: DNA
<213> ORGANISM: Homo sapiens

<400> SEQUENCE: 33
aacaaaaacc ctctaacaag                                                    20

<210> SEQ ID NO 34
<211> LENGTH: 20
<212> TYPE: DNA
<213> ORGANISM: Homo sapiens

<400> SEQUENCE: 34
gcagtaaaac cgaacatatg                                                    20

<210> SEQ ID NO 35
<211> LENGTH: 18
<212> TYPE: DNA
<213> ORGANISM: Homo sapiens

<400> SEQUENCE: 35
tggacttttg ggtgtctg                                                      18

<210> SEQ ID NO 36
<211> LENGTH: 20
<212> TYPE: DNA
<213> ORGANISM: Homo sapiens

<400> SEQUENCE: 36 ctaatacect gcaaatagca                                                    20

<210> SEQ ID NO 37
<211> LENGTH: 19
<212> TYPE: DNA
<213> ORGANISM: Homo sapiens

<400> SEQUENCE: 37
cgccggccac gagaatggt                                                     19

<210> SEQ ID NO 38
<211> LENGTH: 19
<212> TYPE: DNA
<213> ORGANISM: Homo sapiens

<400> SEQUENCE: 38
cgccggccac gagaattgc                                                     19

<210> SEQ ID NO 39
<211> LENGTH: 21
<212> TYPE: DNA
<213> ORGANISM: Homo sapiens

<400> SEQUENCE: 39
agtgcttccc tggaggtgag a                                                  21
```

```
<210> SEQ ID NO 40
<211> LENGTH: 21
<212> TYPE: DNA
<213> ORGANISM: Homo sapiens

<400> SEQUENCE: 40
cttggttgaa atctcctgcc c                                              21

<210> SEQ ID NO 41
<211> LENGTH: 21
<212> TYPE: DNA
<213> ORGANISM: Homo sapiens

<400> SEQUENCE: 41
cttggttgaa atctcctgac t                                              21

<210> SEQ ID NO 42
<211> LENGTH: 19
<212> TYPE: DNA
<213> ORGANISM: Homo sapiens

<400> SEQUENCE: 42
cgagccattg gtgctgatc                                                 19

<210> SEQ ID NO 43
<211> LENGTH: 21
<212> TYPE: DNA
<213> ORGANISM: Homo sapiens

<400> SEQUENCE: 43 gcttttttccg actgcacgca g                                             21

<210> SEQ ID NO 44
<211> LENGTH: 21
<212> TYPE: DNA
<213> ORGANISM: Homo sapiens

<400> SEQUENCE: 44 gcttttttccg actgcacgaa a                                             21

<210> SEQ ID NO 45
<211> LENGTH: 21
<212> TYPE: DNA
<213> ORGANISM: Homo sapiens

<400> SEQUENCE: 45
gcattccagg ctaagcctag c                                              21

<210> SEQ ID NO 46
<211> LENGTH: 27
<212> TYPE: DNA
<213> ORGANISM: Homo sapiens

<400> SEQUENCE: 46
gcgcgcgcgg gcgcaatagc caagccc                                        27

<210> SEQ ID NO 47
<211> LENGTH: 27
<212> TYPE: DNA
<213> ORGANISM: Homo sapiens

<400> SEQUENCE: 47
ccgccccaca agtcgctcgg cggacgc                                        27
```

<210> SEQ ID NO 48
<211> LENGTH: 19
<212> TYPE: DNA
<213> ORGANISM: Homo sapiens

<400> SEQUENCE: 48
gaagctgcgg gagctgaaa                                                   19

<210> SEQ ID NO 49
<211> LENGTH: 19
<212> TYPE: DNA
<213> ORGANISM: Homo sapiens

<400> SEQUENCE: 49
atccccgact gcctgaacc                                                   19

<210> SEQ ID NO 50
<211> LENGTH: 20
<212> TYPE: DNA
<213> ORGANISM: Homo sapiens

<400> SEQUENCE: 50
ctgcatttgg ctgggtcttt                                                  20

<210> SEQ ID NO 51
<211> LENGTH: 20
<212> TYPE: DNA
<213> ORGANISM: Homo sapiens

<400> SEQUENCE: 51
cgcacctggc ccttagtaag                                                  20

<210> SEQ ID NO 52
<211> LENGTH: 20
<212> TYPE: DNA
<213> ORGANISM: Homo sapiens

<400> SEQUENCE: 52
agcctgtgca gggatgattg                                                  20

<210> SEQ ID NO 53
<211> LENGTH: 22
<212> TYPE: DNA
<213> ORGANISM: Homo sapiens

<400> SEQUENCE: 53
caaccccaga tgaggagtta gg                                               22

<210> SEQ ID NO 54
<211> LENGTH: 20
<212> TYPE: DNA
<213> ORGANISM: Homo sapiens

<400> SEQUENCE: 54
ctcatctggg gttgcattga                                                  20

<210> SEQ ID NO 55
<211> LENGTH: 20
<212> TYPE: DNA
<213> ORGANISM: Homo sapiens

<400> SEQUENCE: 55
gggttggcat gaggacactg                                                  20

<210> SEQ ID NO 56
<211> LENGTH: 18
<212> TYPE: DNA
<213> ORGANISM: Homo sapiens

<400> SEQUENCE: 56
gggcaggtca gcagtgtc                                                 18

<210> SEQ ID NO 57
<211> LENGTH: 20
<212> TYPE: DNA
<213> ORGANISM: Homo sapiens

<400> SEQUENCE: 57
tacacccacc ccaaagtaga                                               20

<210> SEQ ID NO 58
<211> LENGTH: 20
<212> TYPE: DNA
<213> ORGANISM: Homo sapiens

<400> SEQUENCE: 58
tactttgggg tgggtgtaga                                               20

<210> SEQ ID NO 59
<211> LENGTH: 20
<212> TYPE: DNA
<213> ORGANISM: Homo sapiens

<400> SEQUENCE: 59
aagagatcac ccgtcagtcc                                               20

<210> SEQ ID NO 60
<211> LENGTH: 20
<212> TYPE: DNA
<213> ORGANISM: Homo sapiens

<400> SEQUENCE: 60
gggactgacg ggtgatctct                                               20

<210> SEQ ID NO 61
<211> LENGTH: 22
<212> TYPE: DNA
<213> ORGANISM: Homo sapiens

<400> SEQUENCE: 61
ttggagtgca agactcaaga tt                                            22

<210> SEQ ID NO 62
<211> LENGTH: 20
<212> TYPE: DNA
<213> ORGANISM: Homo sapiens

<400> SEQUENCE: 62
ccaggagtct tgggtgtctt                                               20

<210> SEQ ID NO 63
<211> LENGTH: 20
<212> TYPE: DNA
<213> ORGANISM: Homo sapiens

<400> SEQUENCE: 63
agaggggcca aagagttagc                                               20

<210> SEQ ID NO 64
<211> LENGTH: 20
<212> TYPE: DNA
<213> ORGANISM: Homo sapiens

<400> SEQUENCE: 64
aactctttgg ccccctctgtg                                              20

<210> SEQ ID NO 65
<211> LENGTH: 21
<212> TYPE: DNA
<213> ORGANISM: Homo sapiens

<400> SEQUENCE: 65
gaagggaaca ctgctgtgaa g                                             21

<210> SEQ ID NO 66
<211> LENGTH: 19
<212> TYPE: DNA
<213> ORGANISM: Homo sapiens

<400> SEQUENCE: 66
gtgcttcagg ggtgtctgc                                                19

<210> SEQ ID NO 67
<211> LENGTH: 22
<212> TYPE: DNA
<213> ORGANISM: Homo sapiens

<400> SEQUENCE: 67
tgtcataggg cagagtcact cc                                            22

<210> SEQ ID NO 68
<211> LENGTH: 22
<212> TYPE: DNA
<213> ORGANISM: Homo sapiens

<400> SEQUENCE: 68
taaggagtga ctctgcccta tg                                            22

<210> SEQ ID NO 69
<211> LENGTH: 18
<212> TYPE: DNA
<213> ORGANISM: Homo sapiens

<400> SEQUENCE: 69
gccaagaggg gctttagg                                                 18

<210> SEQ ID NO 70
<211> LENGTH: 20
<212> TYPE: DNA
<213> ORGANISM: Homo sapiens

<400> SEQUENCE: 70
agcccctctt ggcttgagta                                               20

<210> SEQ ID NO 71
<211> LENGTH: 19
<212> TYPE: DNA
<213> ORGANISM: Homo sapiens

<400> SEQUENCE: 71

```
tgccgattcc ctccattct                                                   19

<210> SEQ ID NO 72
<211> LENGTH: 20
<212> TYPE: DNA
<213> ORGANISM: Homo sapiens

<400> SEQUENCE: 72
agggcagtgg catgagtaac                                                  20

<210> SEQ ID NO 73
<211> LENGTH: 20
<212> TYPE: DNA
<213> ORGANISM: Homo sapiens

<400> SEQUENCE: 73
ggctattccg ctgctcactt                                                  20

<210> SEQ ID NO 74
<211> LENGTH: 21
<212> TYPE: DNA
<213> ORGANISM: Homo sapiens

<400> SEQUENCE: 74
ttggcttttg aggctatatc c                                                21

<210> SEQ ID NO 75
<211> LENGTH: 23
<212> TYPE: DNA
<213> ORGANISM: Homo sapiens

<400> SEQUENCE: 75
catgtaggaa acacaaggaa gta                                              23

<210> SEQ ID NO 76
<211> LENGTH: 21
<212> TYPE: DNA
<213> ORGANISM: Homo sapiens

<400> SEQUENCE: 76
tgaagttaag ggcagaacac c                                                21

<210> SEQ ID NO 77
<211> LENGTH: 22
<212> TYPE: DNA
<213> ORGANISM: Homo sapiens

<400> SEQUENCE: 77
gttcacccag acattcgtta gt                                               22

<210> SEQ ID NO 78
<211> LENGTH: 22
<212> TYPE: DNA
<213> ORGANISM: Homo sapiens

<400> SEQUENCE: 78
aggacaagga gaggattctc tg                                               22

<210> SEQ ID NO 79
<211> LENGTH: 18
<212> TYPE: DNA
<213> ORGANISM: Homo sapiens
```

```
<400> SEQUENCE: 79
ggaatggggg ctttcaga                                            18

<210> SEQ ID NO 80
<211> LENGTH: 17
<212> TYPE: DNA
<213> ORGANISM: Homo sapiens

<400> SEQUENCE: 80
ctttgggcgt cgacgag                                             17

<210> SEQ ID NO 81
<211> LENGTH: 19
<212> TYPE: DNA
<213> ORGANISM: Homo sapiens

<400> SEQUENCE: 81
gaggggacag gcttctcag                                           19

<210> SEQ ID NO 82
<211> LENGTH: 20
<212> TYPE: DNA
<213> ORGANISM: Homo sapiens

<400> SEQUENCE: 82
attgagtgcc agggttgtca                                          20

<210> SEQ ID NO 83
<211> LENGTH: 20
<212> TYPE: DNA
<213> ORGANISM: Homo sapiens

<400> SEQUENCE: 83
cggaacccca gtggtgatac                                          20

<210> SEQ ID NO 84
<211> LENGTH: 20
<212> TYPE: DNA
<213> ORGANISM: Homo sapiens

<400> SEQUENCE: 84
tgtactagcg gatcaagtat                                          20

<210> SEQ ID NO 85
<211> LENGTH: 19
<212> TYPE: DNA
<213> ORGANISM: Homo sapiens

<400> SEQUENCE: 85
tggcaaaact gagtcatag                                           19

<210> SEQ ID NO 86
<211> LENGTH: 22
<212> TYPE: DNA
<213> ORGANISM: Homo sapiens

<400> SEQUENCE: 86
gtctggtgtt gctttctcta ac                                       22

<210> SEQ ID NO 87
<211> LENGTH: 17
<212> TYPE: DNA
<213> ORGANISM: Homo sapiens
```

<400> SEQUENCE: 87
gtgatgcggg cgatgtt                    17

<210> SEQ ID NO 88
<211> LENGTH: 19
<212> TYPE: DNA
<213> ORGANISM: Homo sapiens

<400> SEQUENCE: 88
tctccaggtg tgcgactgc                  19

<210> SEQ ID NO 89
<211> LENGTH: 22
<212> TYPE: DNA
<213> ORGANISM: Homo sapiens

<400> SEQUENCE: 89
aggaagcctt gagaaggtaa cc              22

<210> SEQ ID NO 90
<211> LENGTH: 20
<212> TYPE: DNA
<213> ORGANISM: Homo sapiens

<400> SEQUENCE: 90
ggaagaactt gaagatgcct                 20

<210> SEQ ID NO 91
<211> LENGTH: 18
<212> TYPE: DNA
<213> ORGANISM: Homo sapiens

<400> SEQUENCE: 91
gctcatttcc tgctctcc                   18

<210> SEQ ID NO 92
<211> LENGTH: 17
<212> TYPE: DNA
<213> ORGANISM: Homo sapiens

<400> SEQUENCE: 92
ccggctttgg ggctata                    17

<210> SEQ ID NO 93
<211> LENGTH: 20
<212> TYPE: DNA
<213> ORGANISM: Homo sapiens

<400> SEQUENCE: 93
gtttctacca tcccagccca                 20

<210> SEQ ID NO 94
<211> LENGTH: 20
<212> TYPE: DNA
<213> ORGANISM: Homo sapiens

<400> SEQUENCE: 94
tacttctgtt gatgggtcac                 20

<210> SEQ ID NO 95
<211> LENGTH: 19
<212> TYPE: DNA

```
<213> ORGANISM: Homo sapiens

<400> SEQUENCE: 95
tggaggagag gaaacctag                                                   19

<210> SEQ ID NO 96
<211> LENGTH: 20
<212> TYPE: DNA
<213> ORGANISM: Homo sapiens

<400> SEQUENCE: 96
acctcccaac actgtcacta                                                  20

<210> SEQ ID NO 97
<211> LENGTH: 17
<212> TYPE: DNA
<213> ORGANISM: Homo sapiens

<400> SEQUENCE: 97
ccctccccaa catgaga                                                     17

<210> SEQ ID NO 98
<211> LENGTH: 20
<212> TYPE: DNA
<213> ORGANISM: Homo sapiens

<400> SEQUENCE: 98
ctgtggccca cgcacttgtg                                                  20

<210> SEQ ID NO 99
<211> LENGTH: 22
<212> TYPE: DNA
<213> ORGANISM: Homo sapiens

<400> SEQUENCE: 99
acgtccttgg tccagcagtg gt                                               22

<210> SEQ ID NO 100
<211> LENGTH: 20
<212> TYPE: DNA
<213> ORGANISM: Homo sapiens

<400> SEQUENCE: 100 gagagggat tcacaaggtg                                                   20

<210> SEQ ID NO 101
<211> LENGTH: 20
<212> TYPE: DNA
<213> ORGANISM: Homo sapiens

<400> SEQUENCE: 101
gccattagct ccaggcttac                                                  20

<210> SEQ ID NO 102
<211> LENGTH: 21
<212> TYPE: DNA
<213> ORGANISM: Homo sapiens

<400> SEQUENCE: 102
gcaaggacag agggctttct g                                                21

<210> SEQ ID NO 103
<211> LENGTH: 20
```

```
<212> TYPE: DNA
<213> ORGANISM: Homo sapiens

<400> SEQUENCE: 103
ccagcaggcc atcaactgat                                               20

<210> SEQ ID NO 104
<211> LENGTH: 19
<212> TYPE: DNA
<213> ORGANISM: Homo sapiens

<400> SEQUENCE: 104
gcacgtcatg gctgactct                                                19

<210> SEQ ID NO 105
<211> LENGTH: 19
<212> TYPE: DNA
<213> ORGANISM: Homo sapiens

<400> SEQUENCE: 105
ctgggaaagc cggttctat                                                19

<210> SEQ ID NO 106
<211> LENGTH: 20
<212> TYPE: DNA
<213> ORGANISM: Homo sapiens

<400> SEQUENCE: 106
tccctgggct gtgtgtagat                                               20

<210> SEQ ID NO 107
<211> LENGTH: 19
<212> TYPE: DNA
<213> ORGANISM: Homo sapiens

<400> SEQUENCE: 107
gagatgggac ccgcatagt                                                19

<210> SEQ ID NO 108
<211> LENGTH: 20
<212> TYPE: DNA
<213> ORGANISM: Homo sapiens

<400> SEQUENCE: 108
tgaagtttgg gttgcacctc                                               20

<210> SEQ ID NO 109
<211> LENGTH: 19
<212> TYPE: DNA
<213> ORGANISM: Homo sapiens

<400> SEQUENCE: 109
agatggtttg cggctgttc                                                19

<210> SEQ ID NO 110
<211> LENGTH: 25
<212> TYPE: DNA
<213> ORGANISM: Homo sapiens

<400> SEQUENCE: 110
gctgatccca gcagcaccct tgttt                                         25

<210> SEQ ID NO 111
```

```
<211> LENGTH: 25
<212> TYPE: DNA
<213> ORGANISM: Homo sapiens

<400> SEQUENCE: 111
aatgggggct tcagaggtg tcact                                              25

<210> SEQ ID NO 112
<211> LENGTH: 20
<212> TYPE: DNA
<213> ORGANISM: Homo sapiens

<400> SEQUENCE: 112
gtggtcaact tccccagaaa                                                   20

<210> SEQ ID NO 113
<211> LENGTH: 20
<212> TYPE: DNA
<213> ORGANISM: Homo sapiens

<400> SEQUENCE: 113
ggccagccca tatacttgat                                                   20

<210> SEQ ID NO 114
<211> LENGTH: 19
<212> TYPE: DNA
<213> ORGANISM: Homo sapiens

<400> SEQUENCE: 114
cgccggccac gagaatggt                                                    19

<210> SEQ ID NO 115
<211> LENGTH: 19
<212> TYPE: DNA
<213> ORGANISM: Homo sapiens

<400> SEQUENCE: 115
cgccggccac gagaattgc                                                    19

<210> SEQ ID NO 116
<211> LENGTH: 21
<212> TYPE: DNA
<213> ORGANISM: Homo sapiens

<400> SEQUENCE: 116
agtgcttccc tggaggtgag a                                                 21

<210> SEQ ID NO 117
<211> LENGTH: 21
<212> TYPE: DNA
<213> ORGANISM: Homo sapiens

<400> SEQUENCE: 117
cttggttgaa atctcctgcc c                                                 21

<210> SEQ ID NO 118
<211> LENGTH: 21
<212> TYPE: DNA
<213> ORGANISM: Homo sapiens

<400> SEQUENCE: 118
cttggttgaa atctcctgac t                                                 21
```

```
<210> SEQ ID NO 119
<211> LENGTH: 19
<212> TYPE: DNA
<213> ORGANISM: Homo sapiens

<400> SEQUENCE: 119
cgagccattg gtgctgatc                                              19

<210> SEQ ID NO 120
<211> LENGTH: 21
<212> TYPE: DNA
<213> ORGANISM: Homo sapiens

<400> SEQUENCE: 120
ccagctccca acactggaga c                                           21

<210> SEQ ID NO 121
<211> LENGTH: 21
<212> TYPE: DNA
<213> ORGANISM: Homo sapiens

<400> SEQUENCE: 121
ccagctccca acactggaga g                                           21

<210> SEQ ID NO 122
<211> LENGTH: 20
<212> TYPE: DNA
<213> ORGANISM: Homo sapiens

<400> SEQUENCE: 122
cccaggctgt tccagaacac                                             20

<210> SEQ ID NO 123
<211> LENGTH: 21
<212> TYPE: DNA
<213> ORGANISM: Homo sapiens

<400> SEQUENCE: 123 gcttttccg actgcacgca g                                            21

<210> SEQ ID NO 124
<211> LENGTH: 21
<212> TYPE: DNA
<213> ORGANISM: Homo sapiens

<400> SEQUENCE: 124 gcttttccg actgcacgaa a                                            21

<210> SEQ ID NO 125
<211> LENGTH: 21
<212> TYPE: DNA
<213> ORGANISM: Homo sapiens

<400> SEQUENCE: 125
gcattccagg ctaagcctag c                                           21

<210> SEQ ID NO 126
<211> LENGTH: 7
<212> TYPE: DNA
<213> ORGANISM: Homo sapiens

<400> SEQUENCE: 126 agaagaa                                                           7
```

```
<210> SEQ ID NO 127
<211> LENGTH: 7
<212> TYPE: DNA
<213> ORGANISM: Homo sapiens

<400> SEQUENCE: 127 tgaagaa                                                                    7

<210> SEQ ID NO 128
<211> LENGTH: 7
<212> TYPE: DNA
<213> ORGANISM: Homo sapiens

<400> SEQUENCE: 128 ataagaa                                                                    7

<210> SEQ ID NO 129
<211> LENGTH: 7
<212> TYPE: DNA
<213> ORGANISM: Homo sapiens

<400> SEQUENCE: 129 ttaagaa                                                                    7

<210> SEQ ID NO 130
<211> LENGTH: 7
<212> TYPE: DNA
<213> ORGANISM: Homo sapiens

<400> SEQUENCE: 130 agaataa                                                                    7

<210> SEQ ID NO 131
<211> LENGTH: 7
<212> TYPE: DNA
<213> ORGANISM: Homo sapiens

<400> SEQUENCE: 131 tgaataa                                                                    7

<210> SEQ ID NO 132
<211> LENGTH: 7
<212> TYPE: DNA
<213> ORGANISM: Homo sapiens

<400> SEQUENCE: 132 ataataa                                                                    7

<210> SEQ ID NO 133
<211> LENGTH: 7
<212> TYPE: DNA
<213> ORGANISM: Homo sapiens

<400> SEQUENCE: 133 ttaataa                                                                    7
```

SCREENING METHODS AND SEQUENCES RELATING THERETO

The present invention relates to inherited variations in genes believed to be involved in base excision repair (BER) pathways of humans; to their use in screening patients for defects in BER and thereby for cancers or predisposition to cancers. The invention further relates to screening methods using the variations, and to a diagnostic kit for use in the screening methods.

BER pathways play a major role in the repair of mutations caused by reactive oxygen species that are generated during aerobic metabolism, as described in Nature 362, 709-715 (1993). Oxidative DNA damage has been implicated in the aetiology of degenerative diseases, ageing and cancer (Mutat. Res. 250, 3116 (1991), but evidence linking inherited deficiencies of BER to these diseases has been lacking.

8-Oxo-7,8-dihydrodeoxyguanine (8-oxoG), the most stable product of oxidative DNA damage, is highly mutagenic, since it readily mispairs with A residues (Nature 349, 431-434 (1991)), leading to an increased frequency of spontaneous G:C→T:A transversion mutations in repair-deficient bacteria and yeast cells. In *E. coli*, three enzymes, mutM, mutY and mutT, function synergistically to protect cells from the deleterious effects of guanine oxidation (J Bacteriol. 174, 6321-6325 (199.2)). The mutM DNA glycosylase removes the oxidised base from 8-oxoG:C base pairs in duplex DNA; the mutY DNA glycosylase excises A miscorporated opposite unrepaired 8-oxoG during replication; and mutT is an 8-oxo-dGTPase preventing incorporation of 8-oxo-dGMP into nascent DNA. Human mutM, mutY and mutT homologues have been identified and termed hOGG1 (Proc. Natl. Acad. Sci. (USA) 94, 8016-8020 (1997)), hMYH (J. Bactiol. 178, 3885-3892 (1996)) and hMTH (J. Biol. Chem. 268, 23524-23530 (1993)), respectively. Patent specification no. WO 97/33903 also discloses a human MutY polypeptide and DNA encoding it, together with its potential use in diagnosing a cancer or a susceptibility to a cancer.

Until now, inherited, as distinguished from somatic, defects of BER have not been associated with any human genetic disorder, although mutations of the *Escherichia coli* BER genes mutM and mutY lead to increased G:C→T:A transversions (Proc. Natl. Acad. Sci. (USA) 85, 2709-2713 (1988); J. Bacteriol. 174, 6321-6325 (1992); Mol. Gen. Genet. 239, 72-76 (1993); and Mol. Gen. Genet. 254, 171-178 (1997)).

We now provide evidence that inherited defects of human BER genes might also lead to increased spontaneous (somatic, as opposed to hereditary) G:C→T:A transversions in other genes, which control cellular growth and so predispose the individual to cancer. Such other genes include the APC gene, a known tumour suppressor gene for colorectal adenomas and carcinomas. Somatic mutations of APC have been found to occur in most such cancers. Accordingly, we further provide evidence that inherited defects in human BER genes can indicate a predisposition towards cancers in humans.

We studied a family (hereinafter, 'family N') having multiple colorectal adenomas and carcinoma, and excluded an inherited mutation of APC as is seen in familial adenomatous polyposis (FAP) (Hum Mol Genet 10 721-733 (2001)). Eleven tumours from three affected siblings contained eighteen somatic APC mutations. Fifteen were G:C→T:A transversions, a significantly greater proportion than reported in sporadic or FAP associated tumours. Analysis of hMYH revealed that the siblings were compound heterozygotes for the non-conservative missense variants, Y165C (an A to G substitution at nucleotide 494 in exon 7) and G382D (a G to A substitution at nucleotide 1145 in exon 13). G382D has been identified (by Shinmura K et al in Cancer Letters 166 65-69 (2001)) in lung cancer samples from the tumour itself; however, it was not identified as an inherited change that might be useful in the detection of predisposition towards lung (or any other) cancer.

These two changes affect residues that are conserved in *E. coli* mutY, namely, y82 and g253; y82 lies within the pseudo HhH motif and has been predicted to function in mismatch specificity (Nat Struct Biol 5 1058-1064 (1998)). Assays of adenine glycosylase activity of y82c and g253d mutants with a G:A substrate showed 90- and 6-fold reduction compared to wild type.

These data link the inherited variants in hMYH to the pattern of somatic APC mutation in family N and implicate defective BER in tumour predisposition in humans and other animals. Subsequent studies have revealed additional inherited variants in hMYH. Therefore, we have been able to provide the identity of such inherited variants and a screening method for identifying an individual having a pre-disposition towards having a cancer as a result of inherited variants in the genes involved in BER.

The present invention therefore provides a variant of hMYH, suitable for use in a screening method of the invention, comprising a polypeptide variant selected from:
(i) Y165C, as defined herein [SEQ ID NO:1];
(ii) E466X, as defined herein [SEQ ID NO:3]; and
(iii) Y90X, as defined herein [SEQ ID NO:4].

The present invention further provides a nucleotide sequence corresponding to any one of the above polypeptide variations, being a nucleotide sequence encoding the polypeptide variant of this invention. Specifically, the nucleotide sequence encoding the polypeptide variants Y165C (SEQ ID NO:1), E466X (SEQ ID NO:2) and Y90X (SEQ ID NO:4) are defined herein as SEQ ID NO:130, SEQ ID NO:131 and SEQ ID NO:132, respectively.

Accordingly, the present invention further provides a nucleotide sequence
(a) encoding a polypeptide variant according to the invention;
(b) a sequence substantially homologous to or that hybridises to sequence (a) under stringent conditions; or
(c) a sequence substantially homologous to or that hybridizes under stringent conditions to the sequence (a) or (b) but for the degeneracy of the genetic code; or
(d) an oligonucleotide specific for any of the sequences (a), (b) or (c).

Such homologous sequences as are referred to in (b) and (c) also display the functional and biological activity of the variation according to the invention. Preferably, such homologous sequences are at least 90% identical to the sequence (a).

Preferably, there is provided a variant of hMYH, comprising Y165C, or a nucleotide sequence encoding the polypeptide, as defined herein as SEQ ID NO: 130.

Such polypeptide and corresponding nucleotide variants are herein collectively referred to as 'variations according to this invention'.

Accordingly, the present invention provides a method for diagnosing susceptibility to cancer comprising determining, from a sample derived from a patient, a mutation comprising a variation according to this invention. In particular, there is provided a screening method for identifying an individual having a pre-disposition towards having a cancer, which screening method comprises the steps of:
(a) obtaining a test sample comprising a nucleotide sequence comprised in a gene in a base excision repair (BER) pathway of the individual or an amino acid sequence of a polypeptide expressed thereby; and (b) comparing a region of the test sample sequence with the corresponding region of the wild type sequence, whereby a difference between the test sample sequence and the wild type sequence signifies that the individual is pre-disposed to having the cancer; and wherein the difference comprises a variation according to this invention, or the known G382D-hMYH or the nucleotide sequence encoding it.

For example, where the variant polypeptide sequence is Y165C-hMYH, this means the human MYH protein in which the 165$^{th}$ amino acid (Y in the wild type) is replaced by C. The corresponding difference in the nucleotide sequence means the gene variant, which is the nucleotide sequence coding for the variant polypeptide (protein) sequence. In the case of Y165C-hMYH, the corresponding nucleotide variant is 494A→G-hMYH, which means the human MYH gene in which the 494$^{th}$ base (A in exon 7 in the wild type) is replaced by G, namely SEQ ID NO:130. However, the variant may also comprise the nucleotide sequence encoding the known G382D-hMYH; or the variant may comprise that encoding E466X-hMYH (1396G→T) or Y90X-hMYH (270C→A).

Preferably, the BER pathway gene is hMYH.

Preferably, in the screening method of the invention, the BER pathway gene is involved in the repair of another gene and protects against G:C→T:A transversion mutations in that gene. More preferably, these G:C→T:A transversion mutations occur at regions of the sequence wherein the G is followed by AA in the sequence and therefore comprise GAA→TAA mutations.

The invention therefore further provides an alternative screening method for identifying an individual having an inherited defect in a BER gene and/or hMYH and/or is pre-disposed to having a cancer, which screening method comprises the steps of:

(a) obtaining a test sample comprising a nucleotide sequence comprised in a marker gene of the individual or an amino acid sequence of a polypeptide expressed thereby, the marker gene being a marker for a disease or condition correlated with the presence of a defect in a BER gene and/or hMYH or cancer; and (b) comparing a region of the test sample sequence with the following diagnostic sequence [SEQ ID NO: 2] or a peptide sequence encoded thereby:

5'-X-X1-A-A-X2-A-A-3'    [SEQ ID NO: 2]

wherein X is A or T; X1 is G or T; and X2 is G or A.

whereby identity between the region of the test sample sequence and the diagnostic sequence signifies that the individual has an inherited defect in a BER gene and/or hMYH and/or is pre-disposed to having the cancer.

Another aspect of the invention is a diagnostic sequence suitable for use in the alternative screening method, which sequence comprises:

(a) 5'-X-X1-A-A-X2-A-A-3'    [SEQ ID NO: 2]

wherein X is A or T; X1 is G or T; and X2 is G or A;

(b) a sequence substantially homologous to or that hybridises to sequence (a) under stringent conditions; or (c) a sequence substantially homologous to or that hybridizes under stringent conditions to the sequence (a) or (b) but for the degeneracy of the genetic code; or (d) an oligonucleotide specific for any of the sequences (a), (b) or (c).

Accordingly, this invention further provides for the use of:

(a) a diagnostic sequence according to the invention, or a polypeptide encoded thereby, (b) a sequence substantially homologous to or that hybridises to nucleotide sequence (a) under stringent conditions; or (c) a sequence substantially homologous to or that hybridizes under stringent conditions to the nucleotide sequence (a) or (b) but for the degeneracy of the genetic code; or (d) an oligonucleotide specific for any of the sequences (a), (b) or (c)

in a therapeutic, diagnostic or detection method, especially for the determination of susceptibility to a disease, such as cancer.

Especially preferred is when the damaged gene is a known marker for the cancer, such as APC (a marker for bowel cancer).

Therefore, in the screening method according to the invention, the cancer is most preferably bowel cancer and/or the damaged gene is APC.

In accordance with the above findings, the present invention therefore still further provides for use of:

(a) a BER gene variant, or a polypeptide encoded thereby, selected from variants of this invention and the known G382D-hMYH or the nucleotide sequence encoding it;

(b) a sequence substantially homologous to or that hybridises to nucleotide sequence (a) under stringent conditions; or (c) a sequence substantially homologous to or that hybridizes under stringent conditions to the nucleotide sequence (a) or (b) but for the degeneracy of the genetic code; or (d) an oligonucleotide specific for any of the sequences (a), (b) or (c)

in a therapeutic, diagnostic or detection method.

Preferably, the BER gene is hMYH and therefore a preferred use is of:

(a) a variant of the hMYH gene, or the hMYH polypeptide encoded thereby, selected from variants of this invention and the known G382D-hMYH or the nucleotide sequence encoding it;

(b) a sequence substantially homologous to or that hybridises to nucleotide sequence (a) under stringent conditions; or (c) a sequence substantially homologous to or that hybridizes under stringent conditions to the nucleotide sequence (a) or (b) but for the degeneracy of the genetic code; or (d) an oligonucleotide specific for any of the sequences (a), (b) or (c)

in a therapeutic, diagnostic or detection method.

A particularly preferred use is when the BER gene and/or hMYH is for the determination of susceptibility to a disease, such as cancer. Especially preferred is wherein the corresponding wild type BER pathway gene or wild type hMYH gene acts to protect against G:C→T:A transverse mutations in a cancer marker gene, such as APC.

The present invention further provides a kit suitable for use in carrying out the screening method of the invention, which kit comprises one or more of:

(a) an oligo- or poly-nucleotide having a nucleic acid sequence corresponding to a region of a variant BER gene, which region incorporates at least one variation from the corresponding wild-type sequence selected from a variation according to this invention;

(b) an oligo- or poly-nucleotide having a nucleic acid sequence corresponding to the wild-type sequence in the region specified in (a); and/or (c) one or more reagents suitable for carrying out PCR for amplifying desired regions of the patient's DNA.

A kit suitable for use in carrying out an alternative screening method as described above comprises one or more of:
(a) an oligo- or poly-nucleotide comprising a diagnostic sequence as described herein, or an amino acid sequence encoded thereby;
(b) one or more reagents suitable for carrying out PCR for amplifying desired regions of the patient's DNA; and/or
(c) a 'surrogate marker' that is indicative of or correlated to the presence of a variant of a sequence (a).

Reagents for the kit may include, for example, PCR primers corresponding to the exon of the BER gene, hMYH or a diagnostic sequence according to the invention; and/or primers mentioned herein; and/or other reagents for use in PCR, such as Taq DNA polymerase.

Preferably, any oligonucleotides in the kit comprise in the range of from 5 to 25 base-pairs, such as 10-20 base-pairs for the variant sequences. In any case, the oligonucleotides must be selected so as to be unique for the region selected and not repeated elsewhere in the genome.

Since, in the situation where it is desired to screen for multiple variations, such as in the range of from 15 to 20 or more, a kit comprising up to 40 oligo- or poly-nucleotides or more would be required, in the alternative screening method, therefore, using DNA chip technology, the present invention provides a plurality of oligo- or poly-nucleotides as defined in kit component (a) above immobilised on a solid support.

Other nucleotide detection methods could be used, such as signal amplification methods being pioneered in nanotechnology (such as Q-Dots). Also, single molecule detection methods could be employed (such as STM). In which case, the kit according to this invention may comprise one or more reagents for use in such alternative methods.

Further, suitable, alternative screening methods according to this invention may further comprise obtaining a test sample comprising a BER variant (eg a protein/peptide sequence comprising a variation of hMYH, such as one encoded by a variant of hMYH as identified above) or a peptide sequence encoded by a diagnostic sequence as defined heerein that is identifiable by conventional protein sequence methods (including mass spectroscopy, micro-array analysis, pyrosequencing, etc), and/or antibody-based methods of detection (eg-ELISA), and carrying out one or more such protein sequencing method(s).

Alternatively, the screening method and corresponding kit according to this invention may be based on one or more so-called 'surrogate markers' that are indicative of or correlated to the presence of a variant of a BER gene, hMYH or a diagnostic sequence as defined herein, or the polypeptide encoded thereby, such as proteins/amino acid sequences eg antibodies specific for a BER gene or protein.

Such a "surrogate marker" may therefore comprise:
(a) any biomolecule (including, but not limited to, nucleotides, proteins eg antibodies, sugars, and lipids);
(b) a chemical compound (including, but not limited to, drugs, metabolites thereof, and other chemical compounds); and/or
(c) a physical characteristic, whose absence, presence, or quantity in an individual is measurable and correlated with the presence of a BER gene variant, hMYH or a diagnostic sequence as defined herein, or a protein encoded thereby.

In which alternative cases, the kit according to this invention may comprise one or more reagents for use in such alternative methods.

It will be evident to the person skilled in the art that, throughout the specification unless the context indicates otherwise, the hMYH gene is classified as an example of a BER pathway gene, but even if hMYH was found to act in an alternative pathway, then the screening methods, kits and uses as described herein in relation to a 'BER gene' would nevertheless apply mutatis mutandis to 'hMYH'.

The basis for the invention will now be described in more detail with reference to the following Examples and Figures, in which:

FIG. 1 shows the pedigree of family N. II.1 and II.2 were found to have approximately 50 macroscopically visible adenomas at 59 and 55 years of age. II.3 died following discovery of a colonic adenocarcinoma and an adjacent adenoma at 46 years of age, but without full assessment of the large bowel. II.4-7 were normal on colonoscopic assessment at between 36 and 49 years of age and III.1-III.5 were normal on colonoscopic assessment at between 24 and 33 years of age. APC haplotypes with the intragenic markers E1317Q, S2497L and the closely linked DP1 $(CA)_n$ repeat are shown.

Figure 2A:
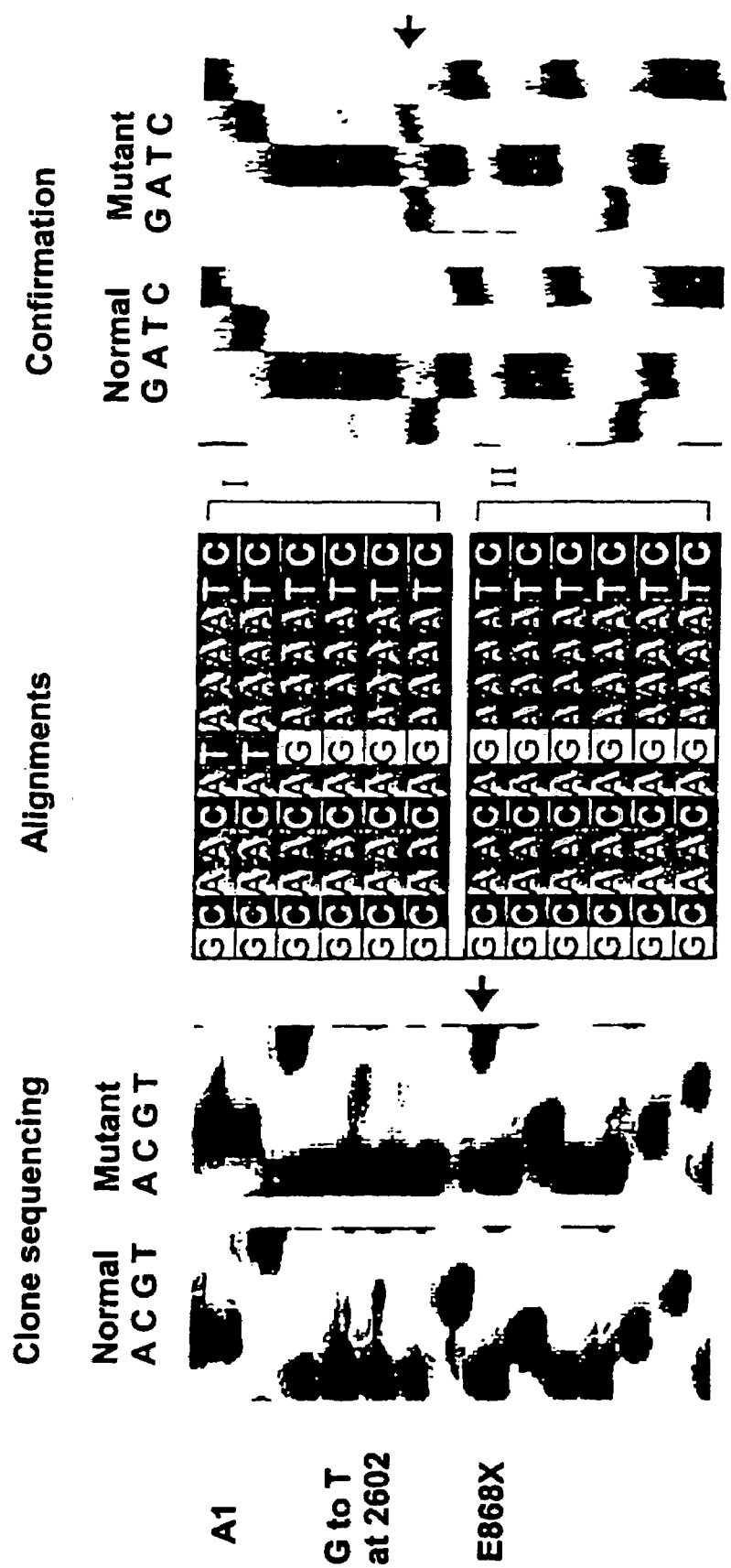
Figure 2B:
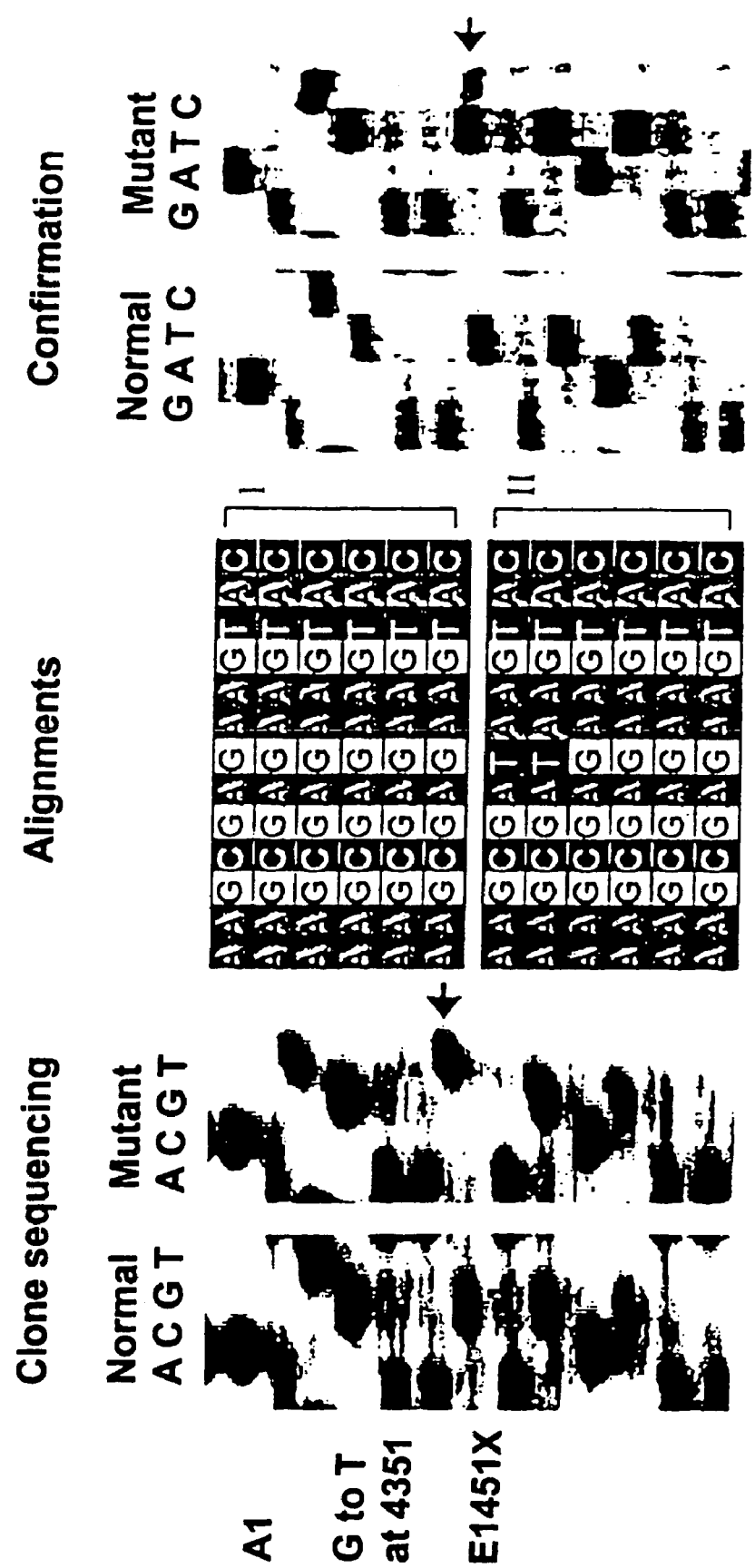
Figure 2C:
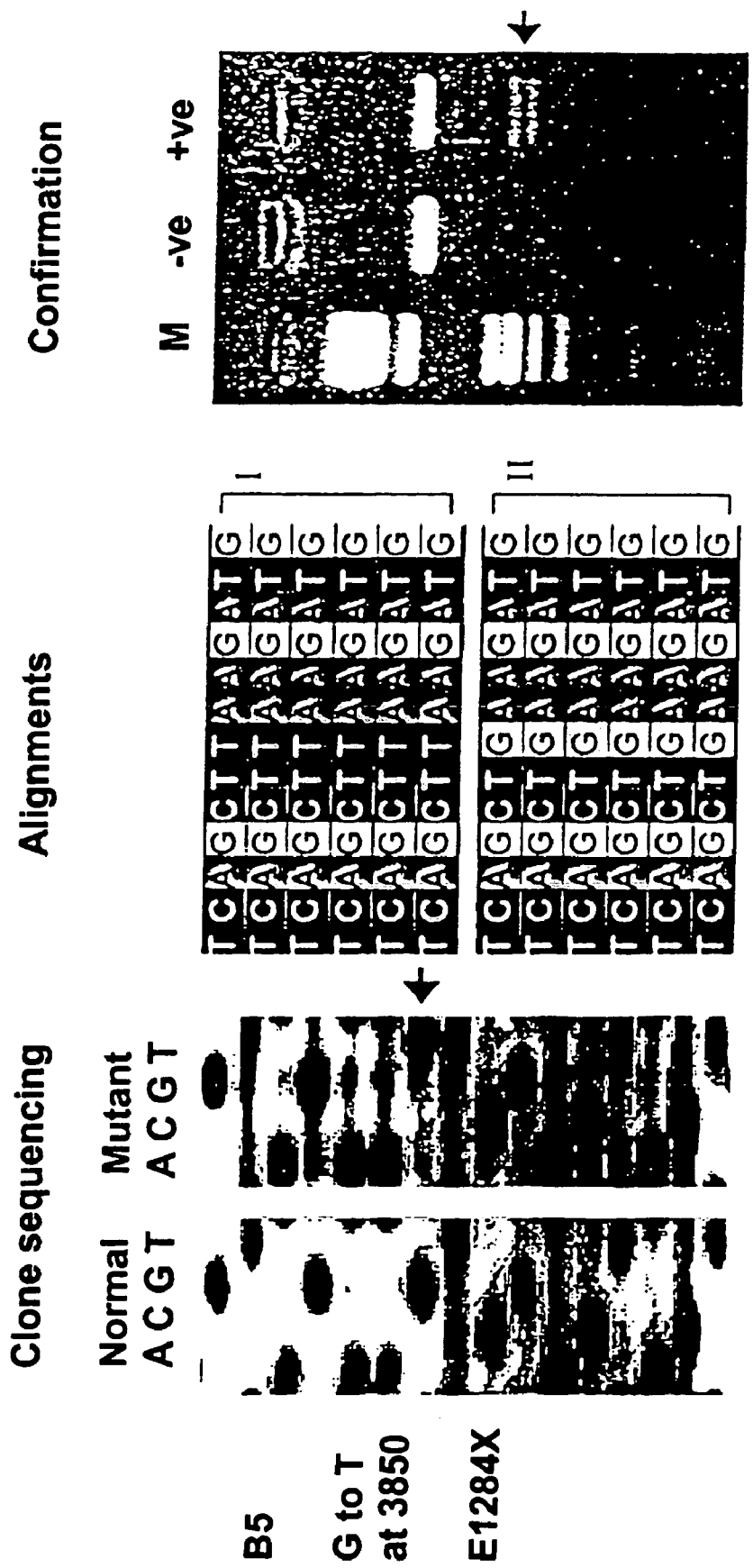

FIG. 2 shows the identification of somatic G:C→T:A mutations of APC in colorectal tumours. Sequences of LD-PCR product clones were aligned. Variants in two or more clones from the same allele (I or II) were confirmed by an independent assay on a fresh PCR product. (a) G>T mutation at position 2602 (E868X) in adenoma A1 confirmed by direct sequencing of standard PCR products. (b) G>T mutation at position 4351 (E1451X) on the second APC allele from adenoma A1 confirmed by direct sequencing of LD-PCR products. (c) G>T mutation at position 3850 (E1284X) in adenoma B5 confirmed by restriction enzyme analysis. Arrows indicate the position of the G:C→T:A mutations on the sequencing gels and the mutant allele on Bfr I cleavage of a PCR product amplified from adenoma B5. M DNA size marker (φ×174 Hae III), −ve wild type control DNA, +ve B5 adenoma DNA.

Figures 3A, 3B:
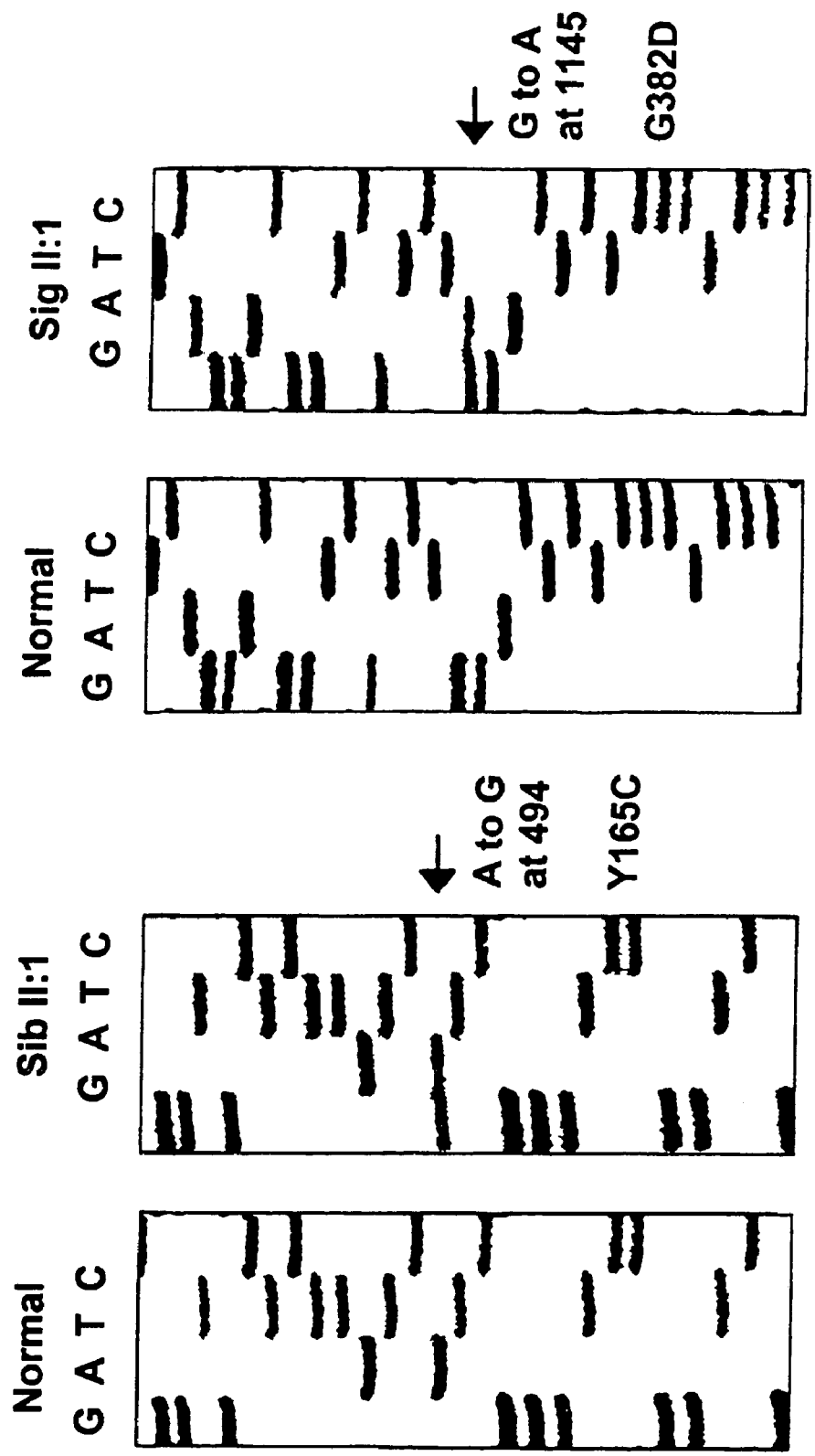
Figure 3C:
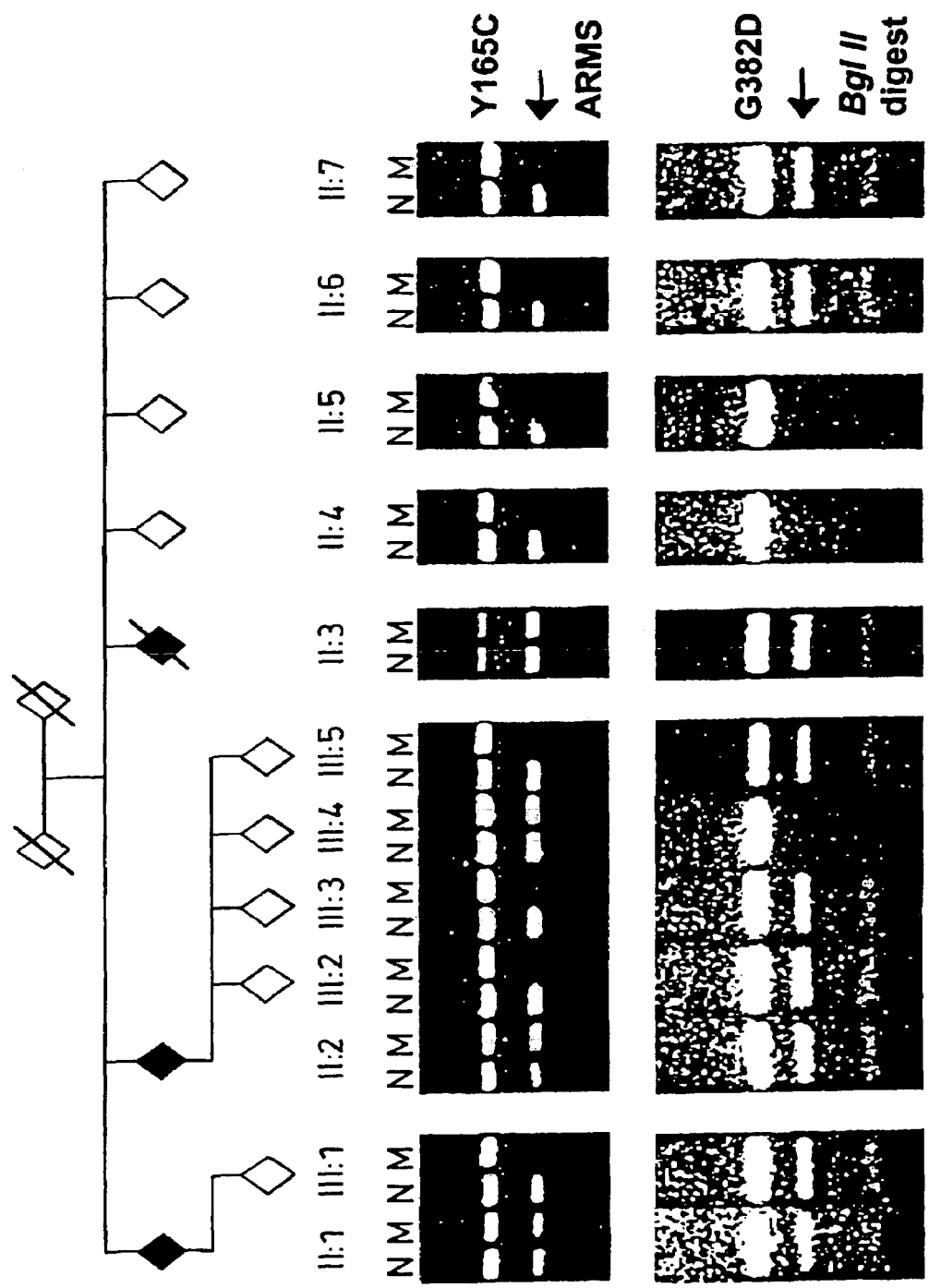

FIG. 3 shows the identification and segregation of germline hMYH variants in family N. Direct sequencing of constitutional DNA from sibling II:1 revealed (a) an A to G substitution at nucleotide 494 in exon 7 corresponding to Y165C (arrow) and (b) a G to A substitution at nucleotide 1145 in exon 13 corresponding to G382D (arrow). (c) Screening for Y165C by ARMS and G382D by a Bgl II digest revealed that the three affected siblings (filled symbols) were compound heterozygotes for these hMYH missense variants, while normal family members (non-filled symbols) were either heterozygous for one of the variants, or normal. N=normal ARMS reaction, M=mutant ARMS reaction. Arrows indicate the positions of the mutant alleles.

FIG. 4 shows the evolutionary conservation of the variant residues in hMYH. Comparison of the variant residues (a) Y165C and (b) G382D in family N with hMYH homologues from *Homo sapiens* (H.sap.), *Mus musculus* (M.mus.), *Arabidopsis thaliana* (A.tha.), *Schizosaccharomyces pombe* (S.pom.), *Hemophilus influenzae* (H.inf.), *Vibrio cholerae* (V.cho.), *Salmonella typhimurium* (S.typ.) and *E. coli* using ClustalW. Arrows indicate the position of the variant residues. Identical, conserved and semi-conserved residues are shaded black, dark grey and light grey respectively. // indicates the position of 18 amino acids in A.tha. that are not present in the other organisms.

Figure 5:
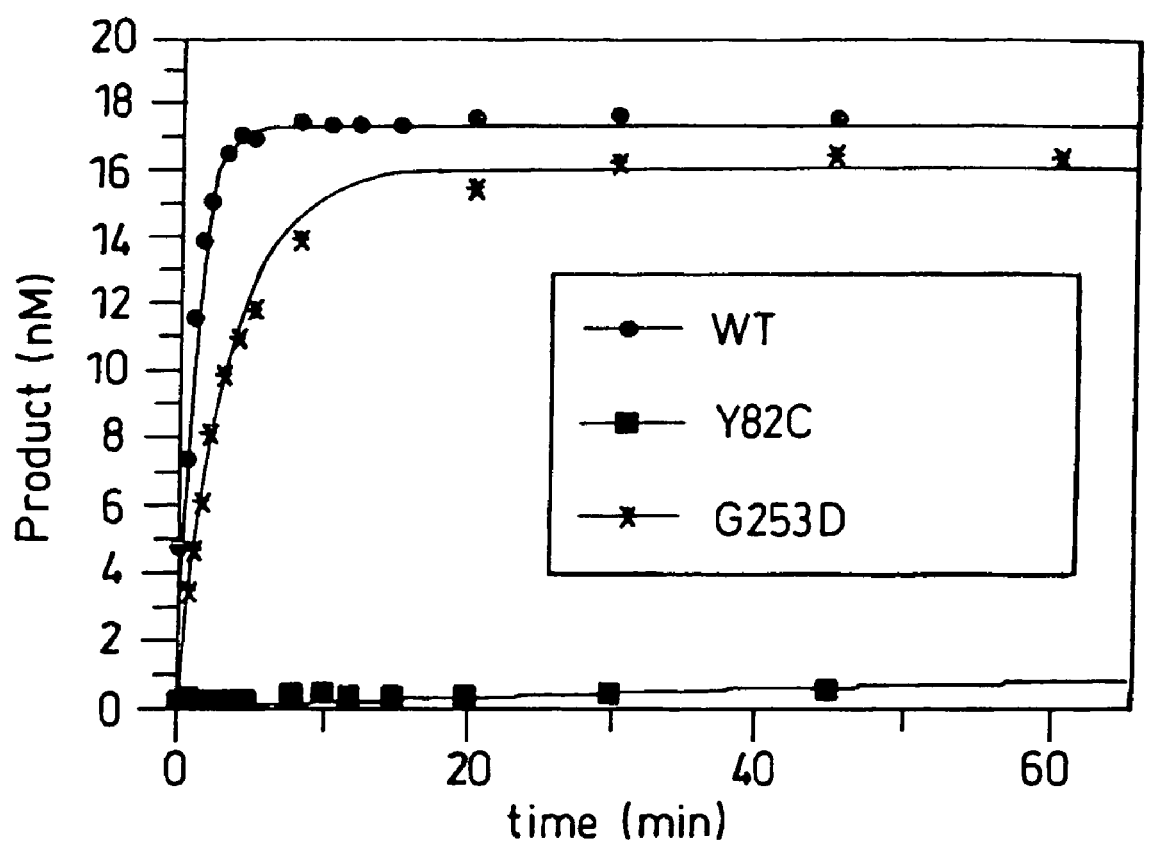

FIG. 5 shows representative plots of single turnover adenine glycosylase assays. Wild type, Y82C, and G253D mutY were assayed for glycosylase activity at 2° C. with a 20 nM duplex DNA substrate containing an 8-oxo G:A mismatch and 30 nM mutY (active site concentration). $k_2$ (min$^{-1}$)=1.6±0.2 for wild type, 0.26±0.05 for G253D and <0.0006 (estimated) for Y82C. All values represent an average of at least four separate determinations and the error is reported as the standard deviation.

EXAMPLE 1

General Methods and Protocols Relating to APC

Samples

Family N: Nucleic Acid was prepared from venous blood samples and from normal colonic mucosa obtained at surgery, using standard methods. Nine colorectal adenomas were obtained at colonoscopy or surgery and one adenoma and a carcinoma were obtained from archived tissues in paraffin blocks. Histopathology was confirmed by independent review. DNA and RNA were prepared from whole tissues that had been snap frozen or from micro-dissected tissue whose nature had been verified histologically on the same or adjacent sections.

Patients with multiple colorectal adenomas: DNA was extracted from venous blood samples from sixteen further unrelated patients with multiple adenomas, with or without co-existing carcinoma. All cases were shown to be normal on sequencing of exon 4 and the alternatively spliced region of exon 9 of APC, mutations in which are associated with AFAP (Hum Mol Genet 10 721-733 (2001). Archived tumour tissue was micro-dissected and DNA extracted using standard methods.

Patients with colorectal cancer: DNA was extracted from venous blood samples using standard methods.

Standard and Long Distance (LD-) PCR and Microsatellite Analysis

Exons 1-3 and 5-14 of APC were amplified using published primers (Cell 66, 589-600 (1991)), and exon 4 was amplified using ex4F (5'-TGCAGTCTTTATTAGCATTGTTT-3' SEQ ID NO:5) and ex4R (5'-TTCAAATAAGTTGTACTGC-CAAG-3' SEQ ID NO:6) which generated a 195bp product. For DNA extracted from paraffin embedded blocks, exon 15 of APC was amplified as 40 overlapping fragments of 162-285bp-Appendix 1. Exons 2-15 of β-catenin (Accession Nos. X89579, 13648651), 2-11 of p53 (Accession No. U94788), 1-16 of hMYH, 1-8 of hOGG1(Accession Nos. AC066599, AC011610) and 2-5 of hMTH (Accession Nos. D38591-4) were amplified as 18, 11, 16, 11 and 4 fragments, respectively. Standard PCR was carried out in 50 µl reaction volumes containing 100 ng genomic DNA, 25 pmole primers, 0.2 mM dNTPs, 5 µreaction buffer and 1U AmpliTaq Gold DNA Polymerase (Applied Biosystems). Cycling parameters were 94° C. 10 mins, followed by 32 cycles of 50-67° C. 1 min, 94° C. 30 secs, and a final step of 72° C. 10 mins. For DNA extracted from fresh tissue, exon 15 of APC was amplified either as a single 6.67 kb LD-PCR fragment using N15F (1997) 5'-GCAAATCCTAAGAGAGAACAACTGT-3' (SEQ ID NO:7') and N15R1(8684) 5'-TCCAGAA-CAAAAACCCTCTAACAAG-3' (SEQ ID NO:8), or as two overlapping LD-PCR fragments using N15F (1997) and NS15 4R (5571) 5'-CCTTCAATAGGCGTGTAATG-3'(SEQ ID NO:9) which generated a 3.59 kb product, and NS15 3F (3649) 5'-AAAGCAGTAAAACCGAACAT-3' (SEQ ID NO:10) and N15R (8698) 5'-TCAAATATGGCTTCCA-GAACAAA-3' (SEQ ID NO:10) which generated a 5.07 kb product. Exons 10 to 16 of hMYH were amplified as a 3.1 kb LD-PCR fragment using Y10F1L (5'-GCTGATCCCAG-CAGCACCCTTGTTT-3' SEQ ID NO:12) and Y16RL (5'-AATGGGGGCTTTCAGAGGTGTCACT-3' SEQ ID NO:13).

The 50 µl LD-PCR reaction mixes contained 100 ng genomic DNA, 10 pmol primers, 0.35 mM dNTPs, 5 µl reaction buffer 3 and 1.75U of Expand Long Template DNA Polymerase (Roche). Cycling parameters were 94° C. 2 mins followed by 33-35 cycles of 56° C. 1 min, 68° C. 4-8 mins (+20 secs per cycle, after cycle number 10) and 94° C. 20 secs, and a final elongation step at 68° C. for 4-8 mins. DNA extracted from normal and tumour tissue was tested for MSI using the markers D2S 123, BAT 26, BAT 24, Mfd15, DP1 (APC), D18S69 and BAT 25.

RT-PCR and Expression Analysis 100 ng-2 µg RNA was used for first strand cDNA synthesis using oligo $(dT)_{15}$ and Superscript II RNase H$^-$ Transcriptase (Invitrogen Life Technologies). Second strand synthesis was carried out in 50 µl reaction volumes using 1 µl cDNA, 25 pmol primers, 0.2 mM dNTPs, 5 µl reaction buffer and 2-5U AmpliTaq Gold DNA Polymerase. Cycling parameters were 94° C. for 10 mins, followed by 35-40 cycles of 94° C. 1 min, 50-54° C. 1 mins, 72° C. 1-3 mins, and a final elongation step at 72° C. for 10 mins. Exons 1-14 of APC were amplified as a 1.958 kb fragment, using the primers previously described (Proc. Natl. Acad. Sci. (USA) 94, 2449-2453 (1997)). To determine the expression levels of individual APC alleles, the exon 11 polymorphism Y486 was assayed in recombinant RT-PCR product clones by restriction digestion or sequence analysis. To characterise aberrant splicing associated with the 423-1G>T somatic mutation, exons 3-12 of APC were amplified by RT-PCR using APCFE>3 (5'-GAGGGTTTG-TAAATGGAAGCAG-3' SEQ ID NO:14) and APCjRE>11-12 (5'-CTCATGCAGCCTTTCATAGAGC-3' SEQ ID NO: 15), cloned and sequenced. To quantify the expression level of the hMYH allele harbouring G382D, normal cobonic mucosa cDNA from sibling II:1 was amplified using rY12F (5'-GTGGTCAACTTCCCCAGAAA-3' SEQ ID NO:16) and rY14R (5'-GGCCAGCCCATATACTTGAT-3' SEQ ID NO:17), cloned and assayed with a Bgl II digest.

Sequencing

Standard PCR products were sequenced manually using the ThermoSequenase cycle sequencing kit (Amersham), and analysed on 6% polyacrylamide gels. For automated plasmid based sequencing, standard, LD- and RT-PCR products were purified using the PCR purification kit (Qiagen), cloned into pGEM-T Easy (Promega), and propogated in JM 109 *E. coli*; at least twelve recombinant clones of each product were sequenced. Automated sequencing of RT-PCR product clones spanning exons 1-14 of APC was performed using two overlapping bi-directional sequencing reactions: (1) NS1$_{13}$ 14F (39) 5'-ATGGCTGCAGCTTCATATGA-3' (SEQ ID NO:18) to NS1$_{13}$ 14R2 (1049) 5'-GCTGTCTTGGGAGCTAGAC-3' (SEQ ID NO:19); (2) NS1$_{13}$ 14F2 (892) 5'-ACCATGAAA-CAGCCAGTGT-3' (SEQ ID NO:20) to NS1$_{13}$ 14R (1978) 5'-CTGTGGTCCTCATTTGTAG-3' (SEQ ID NO:21). Automated sequencing of LD-PCR products and clones spanning exon 15 of APC was performed using eight overlapping bi-directional sequencing reactions: (1) NS15 1F (1997) 5'-GCAAATCCTAAGAGAGAACA-3' (SEQ ID NO:22) to NS15 8R (3146) 5'-GACTTTGCCTTCCAGAGTTC-3' (SEQ ID NO:23); (2) NS15 2F (2810) 5'-AAGCTCTGCT-GCCCATACACA-3' (SEQ ID NO:24) to NS15 7R (3935) 5'-CTGCTATTTGCAGGGTATTA-3' (SEQ ID NO:25); (3) NS15 3F (3649) 5'-AAAGCAGTAAAACCGAACAT-3' (SEQ ID NO:26) to NS15 3R (4775) 5'-TTGTTGGCATG-GCAGAAATA-3' (SEQ ID NO:27); (4) NS15 4F (4480) 5'-TTCTTCCAGATGCTGATACT-3' (SEQ ID NO:28) to NS15 4R (5571) 5'-CCTTCAATAGGCGTGTAATG-3' (SEQ ID NO:29); (5) NS15 5F (5234) 5'-GCCCAAAGG- GAAAAGTCACA-3' (SEQ ID NO:30) to NS15 5R (6346) 5'-ATTTGCACCTTCCTGAATAG-3' (SEQ ID NO:31); (6) NS15 6F (6015) 5'-CCTGACTCACAGGGAGAAC-3' (SEQ ID NO:32) to NS15 6R (7135) 5'-CTGTCTACCTGGAGAT-GTAT-3' (SEQ ID NO:33); (7) NS15 7F (6807) 5'-GCCTC-CAAAAGCCCTAGTGA-3' (SEQ ID NO:34) to NS15 2R (7920) 5'-AGCACCTGAGGAAACGGTCTG-3' (SEQ ID NO:35); (8) NS15 8F (7552) 5'-GAAAACTCCCAC-CTAATCTC-3' (SEQ ID NO:36) to NS15 1R (8684) 5'-AA-CAAAAACCCTCTAACAAG-3' (SEQ ID NO:37).

Primer nucleotide numbers in parentheses are cited according to Science 253, 661-5 (1991). Automated sequencing of LD-PCR product clones spanning exons 10-16 of hMYH, RT-PCR product clones spanning exons 3-12 of APC and 12-14 of hMYH, and standard PCR product clones, was performed using M13 forward and reverse primers, as previously described (Hum. Mol. Genet 9, 1119-1129 (2000)). Sequence data for $\geq 12$ clones was aligned (AlignIR v1.2, Li-Cor) and variants in two or more clones from the same allele were analysed by an independent assay on a fresh PCR product, to confirm that they represented real mutations and were not PCR or cloning induced errors.

Assays for Sequence Variants

In APC: Y486 (1458 C>T) in exon 11 was assayed using an Rsa I digest, as previously described (Cell 66, 589-600 (1991)). E1317Q (3949 G>C) in exon 15 was assayed using a Pvu II digest of a 503 bp PCR product generated using E1317QLF (3652) 5'-GCAGTAAAACCGAACATATG-3' (SEQ ID NO:38) and E1317QR (4137) 5'-TG-GACTTTTGGGTGTCTG-3' (SEQ ID NO:39); DNA from paraffin embedded blocks was assayed using a 224 bp PCR product generated with E1317QSF (3934) 5'-CTAATAC-CCTGCAAATAGCA-3' (SEQ ID NO:40) and E1317QR (4137). A545 (1635 A>G) in exon 13 and T1493 (4479 G>A), A1755 (5265 G>A), S1756 (5268 G>T), and S2497L (7491 C>T) in exon 15, were assayed by sequencing.

The somatic APC mutations E1284X (3850 G>T) and E1317X (3949 G>T) in exon 15 were assayed using a Bfr I digest of PCR products generated with E1317QLF and E1317QR. Somatic APC mutations were assigned to an allele by linking them to one of the polymorphic markers using either standard, RT-, or LD-PCR, followed by cloning and sequencing. The following missense variants in hMYH were assayed in 100 normal control patients: V22M (66 G>A) was assayed using an Nco I digest of exon 2 PCR products. Y165C (494 A>G) in exon 7 was assayed using normal (165N 5'-CGCCGGCCACGAGAATGGT-3' SEQ ID NO:41) or mutant (165M 5'-CGCCGGCCACGAGAATTGC-3' SEQ ID NO:42) specific ARMS primers together with the cominon primer 165C (5'-AGTGCTTCCCTGGAGGTGAGA-3' SEQ ID NO:43). R260Q (779 G>A) in exon 10 was assayed using normal (260N 5'-CTTGGTTGAAATCTCCTGCCC-3' SEQ ID NO:44) or mutant (260M 5'-CTTGGTTGAAATCTCCT-GACT-3' SEQ TD NO:45) specific ARMS primers together with the common primer 260C (5'-CGAGCCATTGGTGCT-GATC-3' SEQ ID NO:46). G382D (1145 G>A) was assayed using a Bgl II digest of exon 13 PCR products. S501 F (1502 C>T) in exon 16 was assayed using normal (501N '-GCTTTTTCCGACTGCACGCAG-3' SEQ ID NO:47) or mutant (501M 5'-GCTTTTTCCGACTGCACGAAA-3' SEQ ID NO:48) specific ARMS primers together with the common primer 501C (5'-GCATTCCAGGCTAAGCCTAGC-3' SEQ ID NO:49). All ARMS reactions incorporated internal control primers (AJ31 and AJ32) to validate the assay. SSCP and dHIPLC analysis at the RTm and RTm+2° C., was carried out as described by Jones et al. (Hum. Genet. 106, 663-668 (2000)).

Somatic APC Mutation Database and Statistical Analysis

We reviewed literature reports of characterised somatic APC mutations in colorectal tumours. This included publications cited in the APC mutation database (Nucleic Acids Res. 24, 121-124 (1996)) and publications from the period 1991-2001 identified through a PubMed (http://www.ncbi.nlm.nih.gov) search. Reports of truncating mutations that were inconsistent with the published cDNA sequence (Science 253, 661-5 (1991)) were excluded, as were putative missense mutations since the evidence for their pathogenicity was inconclusive. Data on 503 somatic mutations observed in sporadic tumours and 308 somatic mutations observed in FAP and AFAP associated tumours was retrieved. This included cases of allelic loss, nonsense, frameshift and splice site mutations at invariant GT-AG dinucleotides. Statistical analysis was carried out using Fisher's Exact test.

Site Directed Mutagenesis (SDM) and Assays of mutY Glycosylase Activity

SDM with the primers y82$c_{13}$ F (5'-GCGCGCGCGGGCGCAATAGCCAAGCCC-3' SEQ ID NO:50) and g253$d_{13}$ F (5'-CCGCCCCACAAGTCGCTCG-GCGGACGC-3' SEQ ID NO:51), cloning, expression and purification of wild type and mutant mutY, was carried out as previously described (Nucleic Acids Res. 29, 553-564 (2001)).

To determine the effect of the y82c and g253d mutations on the intrinsic rate of adenine removal compared to wild type, glycosylase assays were performed under single turnover conditions ([DNA]<[MutY]) as described (Biochem. 37, 14756-14764 (1998)) using a 30 bp duplex containing a centrally-located 8-oxo-G:A or G:A base pair. The amount of active protein (wild type 39%, y82c 53%, g253d 58%) was determined using active site titration methods (Biochem 37, 14756-14764 (1998)). The resulting data were fitted to the single exponential equation: $[P]_t=A_0[1-\exp(-k_{obs}t)]$. Under the conditions used for these experiments, $k_{obs}$ approximates $k_2$ (Biochem 37, 14756-14764 (1-998)).

EXAMPLE 2

Primers, Conditions and Methods for Amplification and Analysis of the Human BER genes hMYH, hOGG1 and hMTH (1) Standard PCR Exons 1-16 of hMYH, 1-8 of hOGG1 (Accession Nos. AC066599, AC011610) and 2-5 of hMTH (Accession Nos. D38591-4) were amplified as 16, 11 and 4 fragments, respectively (Tables 2-4). Standard PCR was carried out in 50 µl reaction volumes containing 100 ng genomic DNA, 25 pmole primers, 0.2 mM dNTPs, 5 µl reaction buffer and 1U Ampli-Taq Gold DNA Polymerase⁻ (Applied Biosystems). Cycling parameters were 94° C. 10 mins, followed by 32 cycles of 50-67° C. 1 min, 72° C. 1 min, 94° C. 30 secs, and a final step of 72° C. 10 mins.

TABLE 2

Primers used for the amplification of hMYH

| Exon | Primer name | Sequence | SEQ ID NO. | Product size | Annealing Temp. |
|---|---|---|---|---|---|
| 1 | Y1F | 5'-GAAGCTGCGGGAGCTGAAA-3' | 52 | 133 bp | 60° C. |
|   | Y1R | 5'-ATCCCCGACTGCCTGAACC-3' | 53 | | |
| 2 | Y2F | 5'-CTGCATTTGGCTGGGTCTTT-3' | 54 | 263 bp | 54° C. |
|   | Y2R | 5'-CGCACCTGGCCCTTAGTAAG-3' | 55 | | |
| 3 | Y3F | 5'-AGCCTGTGCAGGGATGATTG-3' | 56 | 272 bp | 57° C. |
|   | Y3R | 5'-CAACCCCAGATGAGGAGTTAGG-3' | 57 | | |
| 4 | Y4F | 5'-CTCATCTGGGGTTGCATTGA-3' | 58 | 167 bp | 57° C. |
|   | Y4R | 5'-GGGTTGGCATGAGGACACTG-3' | 59 | | |
| 5 | Y5F | 5'-GGGCAGGTCAGCAGTGTC-3' | 60 | 189 bp | 57° C. |
|   | Y5R | 5'-TACACCCACCCCAAAGTAGA-3' | 61 | | |
| 6 | Y6F | 5'-TACTTTGGGGTGGGTGTAGA-3' | 62 | 185 bp | 54° C. |
|   | Y6R | 5'-AAGAGATCACCCGTCAGTCC-3' | 63 | | |
| 7 | Y7F | 5'-GGGACTGACGGGTGATCTCT-3' | 64 | 186 bp | 54° C. |
|   | Y7R | 5'-TTGGAGTGCAAGACTCAAGATT-3' | 65 | | |
| 8 | Y8F | 5'-CCAGGAGTCTTGGGTGTCTT-3' | 66 | 240 bp | 57° C. |
|   | Y8R | 5'-AGAGGGGCCAAAGAGTTAGC-3' | 67 | | |
| 9 | Y9F | 5'-AACTCTTTGGCCCCTCTGTG-3' | 68 | 196 bp | 57° C. |
|   | Y9R | 5'-GAAGGGAACACTGCTGTGAAG-3' | 69 | | |
| 10 | Y10F | 5'-GTGCTTCAGGGGTGTCTGC-3' | 70 | 262 bp | 57° C. |
|   | Y10R | 5'-TGTCATAGGGCAGAGTCACTCC-3' | 71 | | |
| 11 | Y11F | 5'-TAAGGAGTGACTCTGCCCTATG-3' | 72 | 248 bp | 54° C. |
|   | Y11R | 5'-GCCAAGAGGGGCTTTAGG-3' | 73 | | |
| 12 | Y12F | 5'-AGCCCCTCTTGGCTTGAGTA-3' | 74 | 298 bp | 57° C. |
|   | Y12R | 5'-TGCCGATTCCCTCCATTCT-3' | 75 | | |
| 13 | Y13F | 5'-AGGGCAGTGGCATGAGTAAC-3' | 76 | 242 bp | 57° C. |
|   | Y13R | 5'-GGCTATTCCGCTGCTCACTT-3' | 77 | | |
| 14 | Y14F | 5'-TTGGCTTTTGAGGCTATATCC-3' | 78 | 256 bp | 54° C. |
|   | Y14R | 5'-CATGTAGGAAACACAAGGAAGTA-3' | 79 | | |
| 15 | Y15F | 5'-TGAAGTTAAGGGCAGAACACC-3' | 80 | 205 bp | 54° C. |
|   | Y15R | 5'-GTTCACCCAGACATTCGTTAGT-3' | 81 | | |
| 16 | Y16F | 5'-AGGACAAGGAGAGGATTCTCTG-3' | 82 | 224 bp | 54° C. |
|   | Y16R | 5'-GGAATGGGGGCTTTCAGA-3' | 83 | | |

TABLE 3

Primers used for the amplification of hOGG1

| Exon | Primer name | Sequence | SEQ ID NO. | Product size | Annealing Temp. |
|---|---|---|---|---|---|
| 1 | M1F | 5'-CTTTGGGCGTCGACGAG-3' | 84 | 237 bp | 57° C. |
|   | M1R | 5'-GAGGGGACAGGCTTCTCAG-3' | 85 | | |
| 2 | M2F1 | 5'-ATTGAGTGCCAGGGTTGTCA-3' | 86 | 245 bp | 57° C. |
|   | M2R1 | 5'-CGGAACCCCAGTGGTGATAC-3' | 87 | | |
|   | M2F2 | 5'-TGTACTAGCGGATCAAGTAT-3' | 88 | 289 bp | 50° C. |
|   | M2R2 | 5'-TGGCAAAACTGAGTCATAG-3' | 89 | | |
| 3 | M3F1 | 5'-GTCTGGTGTTGCTTTCTCTAAC-3' | 90 | 229 bp | 50° C. |
|   | M3R1 | 5'-GTGATGCGGGCGATGTT-3' | 91 | | |
|   | M3F2 | 5'-TCTCCAGGTGTGCGACTGC-3' | 92 | 275 bp | 57° C. |
|   | M3R2 | 5'-AGGAAGCCTTGAGAAGGTAACC-3' | 93 | | |

TABLE 3-continued

Primers used for the amplification of hOGG1

| Exon | Primer name | Sequence | SEQ ID NO. | Product size | Annealing Temp. |
|---|---|---|---|---|---|
| 4 | M4F | 5'-GGAAGAACTTGAAGATGCCT-3' | 94 | 296 bp | 55° C. |
|   | M4R | 5'-GCTCATTTCCTGCTCTCC-3' | 95 | | |
| 5 | M5F | 5'-CCGGCTTTGGGGCTATA-3' | 96 | 279 bp | 57° C. |
|   | M5R | 5'-GTTTCTACCATCCCAGCCCA-3' | 97 | | |
| 6 | M6F | 5'-TACTTCTGTTGATGGGTCAC-3' | 98 | 153 bp | 55° C. |
|   | M6R | 5'-TGGAGGAGAGGAAACCTAG-3' | 99 | | |
| 7 | M7F | 5'-ACCTCCCAACACTGTCACTA-3' | 100 | 265 bp | 55° C. |
|   | M7R | 5'-CCCTCCCCAACATGAGA-3' | 101 | | |
| 8 | M8F1 | 5'-CTGTGGCCCACGCACTTGTG-3' | 102 | 253 bp | 57° C. |
|   | M8R1 | 5'-ACGTCCTTGGTCCAGCAGTGGT-3' | 103 | | |
|   | M8F2 | 5'-GAGAGGGGATTCACAAGGTG-3' | 104 | 287 bp | 55° C. |
|   | M8R2 | 5'-GCCATTAGCTCCAGGCTTAC-3' | 105 | | |

TABLE 4

Primers used for the amplification of hMTH

| Exon | Primer Name | Sequence | SEQ ID NO. | Product size | Annealing Temp. |
|---|---|---|---|---|---|
| 2 | T2F | 5'-GCAAGGACAGAGGGCTTTCTG-3' | 106 | 249 bp | 67° C. |
|   | T2R | 5'-CCAGCAGGCCATCAACTGAT-3' | 107 | | |
| 3 | T3F | 5'-GCACGTCATGGCTGACTCT-3' | 108 | 246 bp | 57° C. |
|   | T3R | 5'-CTGGGAAAGCCGGTTCTAT-3' | 109 | | |
| 4 | T4F | 5'-TCCCTGGGCTGTGTGTAGAT-3' | 110 | 298 bp | 57° C. |
|   | T4R | 5'-GAGATGGGACCCGCATAGT-3' | 111 | | |
| 5 | T5F | 5'-TGAAGTTTGGGTTGCACCTC-3' | 112 | 281 bp | 57° C. |
|   | T5R | 5'-AGATGGTTTGCGGCTGTTC-3' | 113 | | |

(2) Long-Distance (LD-) PCR

Exons 10 to 16 of hMYH were amplified as a 3.1 kb LD-PCR fragment using Y10F1L (5'-GCTGATCCAG-CAGCACCCTTGTTT-3' SEQ ID NO:114) and Y16RL (5'-AATGGGGGCTTTCAGAGGTGTCACT-3' SEQ ID NO:115). The 50 µl LD-PCR reaction mixes contained 100 ng genomic DNA, 10pmol primers, 0.35 mM dNTPs, 5 µl reaction buffer 3 and 1.75U of Expand Long Template DNA Polymerase (Roche). Cycling parameters were 94° C. 2 mins followed by 33-35 cycles of 56° C. 1 min, 68° C. 4-8 mins (+20 secs per cycle, after cycle number 10) and 94° C. 20 secs, and a final elongation step at 68° C. for 4-8 mins.

(3) RT-PCR and Expression Analysis

100ng-2 µg RNA was used for first strand cDNA synthesis using oligo (dT)$_{15}$ and Superscript II RNase H$^{31}$ Transcriptase (Invitrogen Life Technologies). Second strand synthesis was carried out in 50 µl reaction volumes using 1 µl cDNA, 25 pmol primers, 0.2 mM dNTPs, 5 µl reaction buffer and 2-5U AmpliTaq Gold DNA Polymerase. Cycling parameters were 94° C. for 10 mins, followed by 35-40 cycles of 94° C. 1 min, 50-54° C. 1 min, 72° C. 1-3 mins, and a final elongation step at 72° C. for 10 mins. To quantify the expression level of the hMYH allele harbouring G382D, normal colonic mucosa cDNA from sibling II:1 was amplified using rY12F (5 '-GTGGTCAACTTCCCCAGAAA-3' SEQ ID NO:116) and rY14R (5'- GGCCAGCCCATATACTTGAT-3' SEQ ID NO:117), cloned and assayed with a Bgl II digest.

(4) Sequencing

Standard PCR products were sequenced manually using the ThermoSequenase cycle sequencing kit (Amersham), and analysed on 6% polyacrylamide gels. For automated plasmid based sequencing, standard, LD- and RT-PCR products were purified using the PCR purification kit (Qiagen), cloned into pGEM-T Easy (Promega), and propagated in JM109 E.coli; at least twelve recombinant clones of each product were sequenced. Automated sequencing of LD-PCR product clones spanning exons 10-16 of hMYH, RT-PCR product clones spanning exons 12-14 of hMYH, and standard PCR product clones, was performed using M13 forward and reverse primers.

(5) Single Strand Conformation Polymorphism (SSCP) and Denaturing High Performance Liquid Chromatography (dHPLC) Analysis SSCP and dHPLC analysis at the RTm and RTm+2° C., was carried out as previously described (Hum. Genet. 106, 663-668 (2000)).

(6) Assays for Sequence Variants

The missense variants in hMYH were assayed in 100 normal control patients (Table 5). All ARMS reactions incorpo-

TABLE 5

Assays for missense variants in hMYH

| Variant | Exon | Assay | SEQ ID NO. |
|---|---|---|---|
| V22M (66 G→A) | 2 | NcoI digest | |
| Y165C (494 A→G) | 7 | Normal ARMS (165N 5'-CGCCGGCCACGAGAATGGT-3') | 118 |
| | | Mutant ARMS (165M 5'-CGCCGGCCACGAGAATTGC-3') | 119 |
| | | Common (165C 5'-AGTGCTTCCCTGGAGGTGAGA-3') | 120 |
| R260Q (779 G→A) | 10 | Normal ARMS (260N 5'-CTTGGTTGAAATCTCCTGCCC-3') | 121 |
| | | Mutant ARMS (260M 5'-CTTGGTTGAAATCTCCTGACT-3') | 122 |
| | | Common (260C 5'-CGAGCCATTGGTGCTGATC-3') | 123 |
| H324Q (972 C→G) | 12 | Normal ARMS (324N 5'-CCAGCTCCCAACACTGGAGAC-3') | 124 |
| | | Mutant ARMS (324M 5'-CCAGCTCCCAACACTGGAGAG-3') | 125 |
| | | Common (324C 5'-CCCAGGCTGTTCCAGAACAC-3') | 126 |
| G382D (1145 G→A) | 13 | BglII digest | |
| S501F (1502 C→T) | 16 | Normal ARMS (501N 5'-GCTTTTTCCGACTGCACGCAG-3') | 127 |
| | | Mutant ARMS (501M 5'-GCTTTTTCCGACTGCACGAAA-3') | 128 |
| | | Common (501C 5'-GCATTCCAGGCTAAGCCTAGC-3') | 129 |

EXAMPLE 3

Investigation of and Data from Family N

As summarised above, and using the methods and materials as described in Examples 1 and 2, we investigated a family N in which three siblings (II:1-3) were affected by multiple colorectal adenomas and carcinoma (FIG. 1). This was a Caucasian family but the method is not limited to any particular ethnic grouping. DNA and RNA extracted from normal colonic mucosa from sibling II:1 and DNA extracted from normal colon tissue embedded within a paraffin block from the deceased sibling II:3, was amplified and sequenced for the 8532 bp open reading frame (ORF) of the APC gene (identification and characterisation of the APC gene is described in Cell 66, 589-600 (1991)).

Five silent base substitutions (1458 C>T [Y486], 1635 A>G [A545], 4479 G>A [T1493], 5265 G>A [A1755] and 5268 G>T [S1756], and two missense variants (E1317Q and S2497L) were identified, but no clearly pathogenic change was found. Assays of the variants showed that none were present in all three affected siblings and that their shared wild type APC haplotype was also present in five other family members who were phenotypically normal on colonoscopic assessment (FIG. 1). Sequencing of RT-PCR products of exons 1-14 of APC in sibling II:1 confirmed equal expression of both alleles with alternate splicing of exons 9a and 10a, as previously reported and described in Human Mol Genet 10, 735-740 (2001). These data effectively excluded inactivation of APC as the primary inherited defect in family N.

Inherited mutations of the mismatch repair (MMR) genes cause hereditary non-polyposis colorectal cancer (HNPCC) characterised by micro-satellite instability (MSI) in the associated tumours. Assessment for MSI in DNA extracted from each of the available tumours that included five adenomas from sibling II:1, four adenomas from sibling II:2, and one adenoma and one carcinoma from sibling II:3, revealed instability with only one (Mfd15) of the seven markers tested in a single adenoma. This observation, and the multiple adenoma phenotype, provided evidence against the presence of a MMR gene defect in family N.

Since biallelic inactivation of APC occurs in most colorectal adenomas and carcinomas (Hum Mol Genet 10 721-733 (2001)), we sequenced the APC ORF to identify somatic mutations in each of the 11 tumours obtained from family N. Eighteen mutations were characterised, of which 15 were G:C→T:A transversions, including 14 nonsense changes and one splice site mutation (Table 6 and FIG. 2). The three remaining mutations were two C:G→T:A transitions at CpG dinucleotides and a case of allelic loss (Table 6).

TABLE 6

Somatic APC mutations identified in family N

| Sample¶ Sequence | Nucleotide change | Amino acid change | No. of clones (x/y)¤ | context |
|---|---|---|---|---|
| A1 | 2602 G>T AGAAAAT | E868X | 2/6 | |
| | 4351 G>T AGAAGTA | E1451X | 2/6 | |
| A2 | 721 G>T AGAA'GCA | E241X | NA | |
| | 4381 G>T TGAAAAG | E1461X | 2/6 | |
| A3 | 4717 G>T TGAAATA | E1573X | 4/5 | |
| | NI | NI | | |
| A4 | 423-1 G>T# | NA | 2/2 | NA |
| | 4351 G>T AGAAGTA | E1451X | 6/6 | |
| A5 | 601 G>T GGAAGAA | E201X | NA | |
| | 4348 C>T | R1450X | 3/6 | NA |
| B2 | 3331 G>T AGAAACA | E1111X | 7/10 | |
| | LOH | LOH | | NA |
| B4 | 3586 C>A TGAAAAT | S1196X | 3/7 | |
| | 3856 G>T TGAAATA | E1286X | 4/5 | |
| B5 | 604 G>T AGAACAA | E202X | 3/6 | |
| | 3850 G>T TGAAGAT | E1284X | 6/6 | |
| B6 | 2863 G>T AGAATAC | E955X | 5/7 | |
| | 3949 G>T TGAAGAT | E1317X | 4/6 | |
| C2b | 1495 C>T | R499X | 3/6 | NA |
| | NI | NI | | |
| C1a | NI | NI | | |
| | NI | NI | | |

Five adenomas from sibling II:1 (A1-5), four adenomas from sibling II:2 (B2, 4-6), and one adenoma (C2b) and one carcinoma (C1a) from sibling II:3 were analysed for somatic APC mutations. Mutations were described according to the established nomenclature system. Biallelic mutations were proven to be on opposite alleles in all tumours, except A2 and A5. 423-1 G>T# was shown to cause skipping of exon 4 and predicted to terminate the reading frame at the $7^{th}$ codon of exon 5.

Number of clones, where x represents the number with the mutation and y represents the total number from that allele. In general, mutations were found in only a proportion of clones. Non-mutated clones from the same allele most likely represent contaminating normal tissue. All mutations were confirmed by an independent assay on a fresh PCR product.

Sequence context surrounding the coding region G:C→T:A mutations (underlined) (the sequence of the non-transcribed strand is shown except for S1196X in B4). NA=not applicable; NI=not identified.

The carcinoma did not contain any identified APC mutations despite re-sequencing of the ORF in DNA from a second micro-dissected tumour sample. Sequence analysis of the coding regions of β-catenin and p53 in DNA from this carcinoma also failed to identify any somatic mutations, suggesting involvement of an alternative tumourigenic pathway. We compared the proportion of G:C→T:A transversion mutations detected in tumours from family N to a database of 503 reported somatic APC mutations from sporadic colorectal adenomas and carcinomas and 308 somatic mutations from FAP associated tumours. The excess of G:C→T:A transversions in family N was highly significant (15/18 vs. 49/503, $P=2.77 \times 10^{-12}$ and 15/18 vs. 30/308, $P=7.69 \times 10^{-12}$ respectively).

To determine if an inherited defect in one of the human BER genes (hOGG1, hMYH or hMTH) was responsible for the pattern of somatic G:C→T:A mutations in family N, DNA extracted from peripheral blood lymphocytes from sibling II:1 was amplified and sequenced for the coding regions of hOGG1, hMYH and hMTH. Two amino acid variants were identified in hMYH, Y165C (an A to G substitution at nucleotide 494 in exon 7) and G382D (a G to A substitution at nucleotide 1145 in exon 13) (FIG. 3). No missense variants or other likely pathogenic changes were identified in hOGG1 or hMTH.

Both hMYH variants were assayed in blood DNA samples from all members of family N and 100 Caucasian control individuals with no history of colorectal adenoma or carcinoma. In family N, the three affected siblings were compound heterozygotes for Y165C and G382D and the unaffected family members were either heterozygous for one of these variants or normal (FIG. 3). Each of the missense variants was also identified once in different normal controls. Since the G to A substitution causing G382D was located at the first base in exon 13, its potential affect on splicing and expression was examined. Only 31 of 100 clones obtained by RT-PCR of normal colonic mucosa total RNA from sibling II:1 harboured the G382D allele, although no aberrant splicing could be detected.

Somatic mutations of hMYH were sought in each of the eleven tumours by dHPLC and SSCP analysis of all exons and by screening for allelic loss by assay of the exon 7 and 13 missense variants. No somatic mutations were identified to suggest that hMYH might function as a tumour suppressor in a manner analogous to the MMR genes in HNPCC (Hum. Mol. Genet. 10, 735-740 (2001)). Neither was there clear evidence for the Y165C or G382D variants being dominant to wild type, since heterozygotes for each were phenotypically normal. Rather, the occurrence of the multiple adenoma phenotype in only the three compound heterozygotes suggested transmission as an autosomal recessive trait.

We then searched for germline mutations of hMYH, hOGG1 and hMTH by sequence analysis of their ORFs in sixteen unrelated patients with between 3 and ~50 colorectal adenomas, with or without carcinoma. hMYH mutations were also sought by dHPLC analysis of all exons in forty-two unrelated patients with colorectal cancer diagnosed at 40 years of age or less or with a family history of at least one first degree relative also affected by colorectal cancer. Several frequent missense polymorphisms were identified, S326C in hOGG1 (Oncogene 16, 3219-32225 (1998)), and V22M, H324Q (J. Bactiol. 178, 3885-3892 (1996)), and S501F in hMYH, but their allele frequencies were not significantly different in the patient groups compared to 100 unaffected controls. One case, MA12, with three adenomas and a carcinoma, was a compound heterozygote for the unique hMYH missense variant R260Q (779 G>A) and the S501F polymorphism. Analysis of the APC ORF in the four tumours revealed two G:C→T:A transversions producing nonsense changes (E477X and S1344X), two frame-shift mutations and one case of allelic loss. Other family members were not available for study and the limited number of tumours precluded establishing a meaningful pattern of APC mutation.

Comparison of hMYH homologues in bacteria, yeast, plant and mammals revealed identical or similar amino acids at the positions of the non-conservative missense changes identified in family N (FIG. 4). To gain insight into the functional consequences of the missense variants, we assessed the effects of the equivalent E coli mutY mutations, y82c and g253d, on the intrinsic rate of adenine removal from a centrally located 8-oxo-G:A or G:A mismatch in a 30 bp duplex.

The mutant proteins exhibited significantly slower rates of adenine removal than wild type (FIG. 5). The mutant proteins exhibited approximately ninety-fold (Y82C) and six-fold (G253D) slower rates of adenine removal from the G:A substrate at 37° C. (k2 (min-1)=1.6±0.04 for wild type, 0.04±0.01 for Y82C and 0.22±0.04 for G253D). The high affinity of MutY for 8-oxo-G:A substrates results in reaction rates that are too fast at 37° C. to be measured using our manual methods, and therefore the reaction rates with this duplex were analysed at 4° C. (FIG. 5). The G253D enzyme exhibited a 5-fold decreased rate of adenine removal; while the Y82C enzyme was so severely compromised in its catalytic activity that minimal conversion of substrate to product was observed during the time period that was monitored.

The dramatic effect of the y82c mutation is consistent with the findings of structural studies of mutY (Nat Struct Biol 5 1058-1064 (1998)), which locate y82 within the pseudo-HhH motif (79-gxgyya-84) and suggest a role in mismatch specificity and flipping of adenine into the base specificity pocket. The reduction in activity associated with g253d was similar to that observed with a truncated form of mutY that lacked the C-terminal third of the protein (Nucleic Acids Res. 29, 553-564 (2001)). In the colonic mucosa, the activity of the hMYH G382D allele may be further compromised by the reduced expression we noted on RT-PCR analysis.

The activity of mutY on mismatched DNA substrates is influenced by the immediate sequence context, and methylation interference experiments have shown that mutY interacts with purines including the G:A mismatched bases and two bases each side (J Biol Chem 270 23582-23588 (1995)). Examination of the sequence surrounding the 14 coding region G:C→T:A mutations in family N revealed that the two bases immediately 3' to the mutated G were always AA. Furthermore, 13/14 sites matched three or all bases in a sequence extending one base 5' (A/T) and three bases 3' (G/A,A,A) to the mutated GAA (Table 6).

Inherited factors are thought to play a major role in at least 15% of colorectal cancer cases, but established predisposition genes account only for a minority of these (Cell 87, 159-170 (1996)). The sub-polymorphic frequency of the hMYH variants identified in family N, and the lack of evidence for pathogenic variants in the other multiple adenoma and colorectal cancer cases studied here, suggest that inherited defects of hMYH will prove to be an uncommon cause of colorectal tumour predisposition. The multiple adenoma phenotype in members of family N may reflect the number of somatic mutations required for initiation of adenoma development. Patients with FAP develop hundreds or thousands of adenomas, each requiring only a single somatic APC mutation. The compound heterozygotes in family N may be more comparable to patients with attenuated FAP (AFAP) who develop smaller numbers of adenomas that require two somatic APC mutations for tumour initiation (Nat. Genet. 20, 385-388 (1998)). By contrast, patients with HNPCC develop only one or a few adenomas or carcinomas that require somatic inactivation of a wild type MMR allele and two somatic APC mutations.

EXAMPLE 4

Investigation of and Data from Seven Unrelated Patients

This example describes the identification of seven further, unrelated patients having multiple colo-rectal adenomas and biallelic germline MYH mutations, including four cases homozygous for truncating mutations. Colo-rectal tumours from these individuals exhibit a significant excess of somatic G:C→T:A mutations, as compared to sporadic and FAP-associated tumours, confirming that biallelic mutations in MYH predispose to CRC.

Methods

Samples

Seventeen unrelated cases of British descent and four unrelated-cases of Indian or Pakistani descent, each having multiple colo-rectal adenomas and/or carcinoma were analysed. DNA was prepared from venous blood samples, and from adenoma and carcinoma tissue from colon that had been micro-dissected from paraffin blocks. The nature of all tissues was verified histologically.

PCR Amplification

Exons 4 and 9 of APC, 1-16 of MYH, 1-8 of OGGJ and 2-5 of MTHJ as 2, 16, 11 and 4 fragments, were amplified as previously described (Al-Tassan et al, Nat Genet 30 227-232 (2002)). A ~2.8 kb segment of APC (between codons 653 and 1589) was amplified, which encompassed the somatic mutation cluster region, as eighteen overlapping fragments. Primer sequences are presented in Appendix 1.

Denaturing High Performance Liquid Chromatography (dH-PLC) Analysis and Fraction Collection dHPLC was carried out using the 3500HT WAVE nucleic acid fragment analysis system (Transgenomic Ltd, Crewe Hall Weston Road, Crewe CW16UZ, UK). To enhance the formation of heteroduplexes prior to analysis, the PCR products were denatured at 94° C. and re-annealed by cooling to 50° C. at a rate of 1° C. per minute. dHPLC was carried out at the melting temperatures predicted by Wavemaker (version 4.1) software (Transgenomic) with a 12% acetonitrile (ACN) gradient over 3 minutes. Samples displaying aberrant dHPLC elution profiles were sequenced directly; those samples without clear sequence variations were re-analysed by isolating and sequencing dHPLC separated heteroduplexes. Fraction collection of heteroduplexes was carried out using a Transgenomic FCW-200 in-line fragment collector and products were eluted in 8% CAN.

Automated Sequencing

Amplification products were purified using the PCR purification kit (Qiagen, 28159 Avenue Stanford, Valencia, Calif. 91355, USA) and automated sequencing was carried out using the Big Dye Terminator Cycle Sequencing kit (Applied Biosystems [ABI], Applied Biosystems, 850 Lincoln Center Drive, Foster City, Calif. 94404, USA) according to the manufacturer's instructions. Sequencing reactions were purified by isopropanol precipitation and analysed on an ABI PRISM 3100 Genetic Analyser. Mutations were described according to the established nomenclature system (Antonarakis et al, Hum Mat 11 1-3 (1998)).

Assays for Sequence Variants

All germline mutations in MYH and somatic mutations in APC were confirmed by sequencing two independent PCR products and/or dHPLC separated heteroduplexes, in forward and/or reverse directions. The germline mutations Y90X, G382D and E466X in MYH were further confirmed by restriction enzyme digestion (using RsaI, BglII and ApoI, respectively). The common polymorphism 972 C>G (H324Q) in exon 12 of MYH was assayed by sequencing.

Somatic APC Mutation Database and Statistical Analysis

A database of 503 somatic mutations observed in sporadic colo-rectal tumours, and 308 somatic mutations observed in FAP and AFAP associated colo-rectal tumours was compiled (Al-Tassan et al Nat Genet 30 227-232 (2002) and Example 1). Statistical analyses were carried out using Fisher's Exact and the chi-squared tests.

Results

Biallelic Germline Mutations in MYH

No germline APC truncating mutations were identified. Sequencing of the entire open reading frame (ORF) of MYH in these cases revealed seven patients with biallelic mutations (Table 7), six of which were presumed to be homozygous for MYH variants since no wild type allele could be detected upon sequence analysis.

One Pakistani case (MA27) was homozygous for the exon 3 nonsense mutation Y90X (270 C>A); two British cases (MA22 and MA34) were homozygous for the exon 7 missense mutation Y165C (494 A>G); one British case (MA25) was compound heterozygous for Y165C/G382D (1145 G>A); and three Indian cases (MA20, MA24 and MA26) were homozygous for the exon 14 nonsense mutation E466X (1396 G>T). No samples were available from any of the parents of these patients, all of whom were unaffected, or any other family members. No patients carried single mutant MYH alleles.

The recurrent MYH variants Y90X (2 mutations) and Y165C (5 mutations) were found in association with the G allele of the exon 12 polymorphism 972 C>G (H324Q), and the recurrent variant E466X (6 mutations) was always found in association with the C allele. Sequencing of the entire ORFs of OGG1 and MTH1 in the fourteen MYH negative cases did not identify any likely pathogenic changes.

TABLE 7

Biallelic germline MYH mutations in patients with multiple colo-rectal adenomas

| Patient | Exon | Nucleotide Change | Amino Acid Change | Ethnic Background |
|---|---|---|---|---|
| MA27 | 3 | 270 C > A | Y90X | Pakistani |
|  | 3 | 270 C > A | Y90X |  |
| MA22 | 7 | 494 A > G | Y165C | British |
|  | 7 | 494 A > G | Y165C |  |
| MA34 | 7 | 494 A > G | Y165C | British |
|  | 7 | 494 A > G | Y165C |  |
| MA25 | 7 | 494 A > G | Y165C | British |
|  | 13 | 1145 G > A | G382D |  |
| MA20 | 14 | 1396 G > T | E466X | Indian |
|  | 14 | 1396 G > T | E466X |  |
| MA24 | 14 | 1396 G > T | E466X | Indian |
|  | 14 | 1396 G > T | E466X |  |
| MA26 | 14 | 1396 G > T | E466X | Indian |
|  | 14 | 1396 G > T | E466X |  |

Identification of Somatic G:C→T:A Mutations in Colo-Rectal Tumours

Using denaturing high performance liquid chromatography (dHPLC) analysis, we sought somatic mutations in the APC gene in colo-rectal tumours isolated from the patients with biallelic germline MYH mutations.

A region of APC was screened, spanning codons 653 to 1589 which encompassed the mutation cluster region (MCR, codons 1286 to 1513, Miyoshi et al, Hum Mol Genet 1 229-233 (1992)), a known hotspot for somatic mutations (Fearnhead et al, Hum Mol Genet 10 721-733 (2001)). In total, 50 somatic mutations were identified of which 49 were G:C→T:A transversion mutations.

The proportion of somatic G:C→T:A transversion mutations in APC that were detected in colo-rectal tumours from patients with biallelic MYH mutations were compared to a database of 503 reported somatic APC mutations from sporadic colo-rectal adenomas and carcinomas, and 308 somatic mutations from FAP associated colo-rectal tumours. The excess of somatic G:C→T:A transversions in patients with biallelic MYH mutations was highly significant.

Sequence Surrounding the somatic G:C→T:A mutations

Examination of the sequence context surrounding the somatic G:C→T:A mutations revealed that the two bases immediately 3' to the mutated G were always AA, irrespective of the nature of the germline MYH mutations. The preponderance of G:C→T:A mutations at GAA sequences is highly significant, since other sequences that could undergo G:C→T:A mutation to stop codons are equally prevalent in the APC coding region (216 GAA sites vs 213 non-GAA sites, $\chi^2=13.28$, $P=2.7>10^{-4}$).

Conclusions

In this study, another patient compound heterozygous for Y165C/G382D and two patients homozygous for Y165C have been identified. More significantly, four unrelated patients homozygous for nonsense mutations in MYH have been identified. Homozygosity for MYH variants (as opposed to a point mutation on one allele and a large deletion on the other allele) is considered highly likely, since one of the six patients was shown to be from a family with known consanguinity, and four patients were from Indian families, which are known to have a high frequency of first and second cousin marriages. None of the patients harboured truncating mutations in exon 4 or the alternatively spliced region of exon 9 of APC, which would have been consistent with AFAP, and none of the parents who carried single mutant MYH alleles, showed signs of CRC. Therefore, these data unequivocally confirm that biallelic inactivation of MYH predisposes to colo-rectal adenoma and carcinoma.

The recurrent mutations Y90X, Y165C and E466X cannot be readily explained in terms of the well characterised mechanisms of hypermutagenesis, and are associated with specific (and different) alleles of the polymorphism 972 C>G in exon 12 of MYH. These mutations are therefore probably not independent mutational events, but derived from the same ancestoral chromosomes. In total, four British families that are either homozygous for Y165C or compound heterozygous for Y165C/G382D, three Indian families that are homozygous for E466X and a single Indian or Pakistani family that is homozygous for Y90X have been identified. Different mutations in MYH may therefore be more frequent in different ethnic populations, consistent with founder effects, and diagnostic screening strategies may have to be optimised accordingly.

In this study, an unusually high frequency of somatic G:C→T:A mutations was observed in colo-rectal tumours from patients with biallelic MYH mutations, and this confirms the pathogenicity of the germline variants.

Together with the earlier study, likely pathogenic variants in the BER genes OGG1 or MTH1 have not been detected in over thirty cases with multiple colo-rectal adenoma and carcinoma.

In conclusion, the above Example provides evidence for a novel autosomal recessive colo-rectal tumour pre-disposition syndrome, and this is the first reported inherited disorder of base excision repair in humans.

APPENDIX 1

TABLE 1

Primers used for the amplification of exon 4 of APC.

| Primer name | Sequence |
|---|---|
| ex4F | 5'-TGCAGTCTTTATTAGCATTGTTT-3' |
| ex4R | 5'-TTCAAATAAGTTGTACTGCCAAG-3' |

TABLE 2

Primers used for the amplification of exon 15 of APC for DNA extracted from paraffin embedded tissue. The nucleotide numbers in the primer names are cited according to Accession number NM_000038 (Kinzler et al. 1991, Josyln et al. 1991). All primers were used at an annealing temperature of 50° C.

| Primer name | Sequence | Product size |
|---|---|---|
| APCintron14F1 | 5'-CTTCTATCCTTTTATTTGCTTGTT-3' | 232 bp |
| APC2136R1 | 5'-GCTAACTGCCCCCATGTC-3' |  |
| APC2113F2 | 5'-CTAAAGACCAGGAAGCATTATG-3' | 281 bp |
| APC2375R2 | 5'-ATGAGATGCCTTTGGGACTT-3' |  |
| APC2327F3 | 5'-ATTAGATGCTCAGCACTTATCAGA-3' | 221 bp |
| APC2526R3 | 5'-ATGAAGAGGAGCTGGGTAACAC-3' |  |
| APC2486F4 | 5'-TGGCAACATGACTGTCCTTTCA-3' | 242 bp |
| APC2706R4 | 5'-TGGCTGACACTTCTTCCATGAC-3' |  |
| APC2657F5 | 5'-TTCAAAGCGAGGTTTGCAGATC-3' | 177 bp |
| APC2812R5 | 5'-GAATGTGTATGGGCAGCAGAGC-3' |  |
| APC2785F6 | 5'-CAGATGAGAGAAATGCACTTAGAA-3' | 204 bp |
| APC2968R6 | 5'-CAATCGAGGGTTTCATTTTGAC-3' |  |
| APC2884F7 | 5'-TGCCTTATGCCAAATTAGAATA-3' | 162 bp |
| APC3027R7 | 5'-CGGCTGGGTATTGACCATA-3' |  |
| APC2968F8 | 5'-GTCAAATGAAACCCTCGATTGA-3' | 195 bp |
| APC3141R8 | 5'-TTTGCCTTCCAGAGTTCAACTG-3' |  |

TABLE 2-continued

Primers used for the amplification of exon 15 of APC for DNA extracted from paraffin embedded tissue. The nucleotide numbers in the primer names are cited according to Accession number NM_000038 (Kinzler et al. 1991, Josyln et al. 1991). All primers were used at an annealing temperature of 50° C.

| Primer name | Sequence | Product size |
| --- | --- | --- |
| APC3047F9 | 5'-CCTAGCCCATAAAATACATAGTGC-3' | 212 bp |
| APC3235R9 | 5'-TTGTACTTTGATTCCTTGATTGTC-3' | |
| APC3182F10 | 5'-ATGGGCAAGACCCAAACACATA-3' | 204 bp |
| APC3363R10 | 5'-CCCACTCGATTTGTTTCTGAACC-3' | |
| APC3332F11 | 5'-TGTTTCTCCATACAGGTCACG-3' | 240 bp |
| APC3551R11 | 5'-TCAATAGGCTGATCCACATGA-3' | |
| APC3460F12 | 5'-CCAATTATAGTGAACGTTACTCTG-3' | 247 bp |
| APC3686R12 | 5'-GATGAAGGTGTGGACGTATTC-3' | |
| APC3648F13 | 5'-CAAAGCAGTAAAACCGAACAT-3' | 277 bp |
| APC3903R13 | 5'-CTTCCTGTGTCGTCTGATTACA-3' | |
| APC3871F14 | 5'-CATCTTTGTCATCAGCTGAAGA-3' | 263 bp |
| APC4114R14 | 5'-ACCACTTTTGGAGGGAGATT-3' | |
| APC4001F15 | 5'-CGAAGTTCCAGCAGTGTCAC-3' | 245 bp |
| APC4227R15 | 5'-TGGCAATCGAACGACTCTC-3' | |
| APC4167F16 | 5'-GTTCAGGAGACCCCACTCAT-3' | 260 bp |
| APC4405R16 | 5'-CTCTTTTCAGCAGTAGGTGCTT-3' | |
| APC4379F17 | 5'-AACCAAGCGAGAAGTACCTAA-3' | 275 bp |
| APC4633R17 | 5'-ATTCTGTTTCATTCCCATTGT-3' | |
| APC4540F18 | 5'-CTTGTTCATCCAGCCTGAGT-3' | 265 bp |
| APC4786R18 | 5'-CGTGATGACTTTGTTGGCA-3' | |
| APC4658F19 | 5'-GCAGCCTAAAGAATCAAATGA-3' | 258 bp |
| APC4895R19 | 5'-GGTTGCAACCTGTTTTGTGAT-3' | |
| APC4850F27 | 5'-TGTGGCAAGGAAACCAAGTC-3' | 273 bp |
| APC5100R27 | 5'-CTGCCTTCTGTAGGAATGGTATC-3' | |
| APC5067F28 | 5'-GGAGGAGCACAGTCAGGTGA-3' | 245 bp |
| APC5292R28 | 5'-GAAGACGACGCAGATGCTTG-3' | |
| APC5251F29 | 5'-ACAAGCCTTTCCGTCTGTGA-3' | 217 bp |
| APC5445R29 | 5'-TCTTTGTTGTCTGAGAAAACTCT-3' | |
| APC5344F30 | 5'-AAAAGAAACCAACTTCACCAGT-3' | 248 bp |
| APC5571R30 | 5'-TCCTTCAATAGGCGTGTAATG-3' | |
| APC5550F31 | 5'-TTTGCTTTTGATTCACCTCA-3' | 262 bp |
| APC5791R31 | 5'-GTTTAGGCTGACCTCGATTTA-3' | |
| APC5709F32 | 5'-GAGGCTAAAGTTACCAGCCAC-3' | 266 bp |
| APC5953R32 | 5'-TTTTCTTGGTCAATGTCACTGA-3' | |
| APC5911F33 | 5'-ATACTCCAGTTTGCTTTTCTCAT-3' | 244 bp |
| APC6133R33 | 5'-AACAGGTCATCTTCAGAGTCAA-3' | |
| APC6049F34 | 5'-CATCAGGCTATGCTCCTAAAT-3' | 279 bp |
| APC6307R34 | 5'-CTGAATCAGGGGATAGACCAT-3' | |
| APC6239F35 | 5'-TATGGGTGGCATATTAGGTGA-3' | 246 bp |
| APC6465R35 | 5'-TGAAATGGTGATCCCAGAGA-3' | |
| APC6414F36 | 5'-AGACAAGCTTCGTCTGATTCA-3' | 264 bp |
| APC6658R36 | 5'-CATTTGGCCTGAAATTTCTG-3' | |
| APC6527F37 | 5'-AGGCCCACGAATTCTAAAA-3' | 247 bp |
| APC6751R37 | 5'-AGGACTTGTACTTGAGGAGCTAT-3' | |
| APC6726F38 | 5'-ATGATTCATATTCCAGGAGTTCG-3' | 261 bp |
| APC6970R38 | 5'-TGGTTGCTGGGCAGGTC-3' | |
| APC6942F39 | 5'-TCAGGATCTAGAGATTCGACCC-3' | 220 bp |
| APC7141R39 | 5'-GGCTCATCTGTCTACCTGGAG-3' | |
| APC7100F40 | 5'-TTCAACTAAGTCCTCAGGTTCT-3' | 269 bp |
| APC7348R40 | 5'-TGAAAGTTGAGTGGCGTACTA-3' | |
| APC7309F41 | 5'-CAAGTGGAAGTGAATCTGATAGA-3' | 240 bp |
| APC7531R41 | 5'-ATCCACCAGCCTGAACAG-3' | |
| APC7463F42 | 5'-TAGGTCCAGGCACAAACTC-3' | 262 bp |
| APC7705R42 | 5'-GCTTACTCGAGGAAGGGATG-3' | |
| APC7683F43 | 5'-CGTGAGCACAGCAAACATTC-3' | 256 bp |
| APC7920R43 | 5'-CACCTGAGGAAACGGTCTG-3' | |
| APC7852F44 | 5'-AAGTATCCGCAAAAGGAACAT-3' | 238 bp |
| APC8072R44 | 5'-TCAATCACGGGGGAGTA-3' | |
| APC8025F45 | 5'-GACTGTCCCATTAACAATCCTAG-3' | 238 bp |
| APC8241R45 | 5'-GTCCTGGTTTTATCTCAGTTCC-3' | |
| APC8165F46 | 5'-CAGTGTTCCCATGCGTACC-3' | 263 bp |
| APC8407R46 | 5'-TATCTGCGCTGCTTTTCCTAG-3' | |
| APC8371F47 | 5'-CTGCCAGAGTGACTCCTTTT-3' | 285 bp |
| APC8632R47 | 5'-TCTTTTAAAGTTTCATTTGAAACA-3' | |

TABLE 3

Primers used for the amplification of CTNNB1. All primers were used at an annealing temperature of 50° C.

| Exon | Name | Primer sequence | Product size |
| --- | --- | --- | --- |
| 2 | b cat2F | 5'-AGGTCTGCGTTTCACTAACCT-3' | 244 bp |
| | b cat2R | 5'-AGCCCCAATTCAGTAACTAAAG-3' | |
| 3 | b cat3F1 | 5'-CATCTGCTTTCTTGGCTGTC-3' | 280 bp |
| | b cat3R1 | 5'-AGGATTGCCTTTACCACTCAG-3' | |
| | b cat3F2 | 5'-GTTAGTCACTGGCAGCAACAG-3' | 230 bp |
| | b cat3R2 | 5'-CTCAAAACTGCATTCTGACTTTC-3' | |
| 4 | b cat4F1 | 5'-TGCTGAACTGTGGATAGTGAGTG-3' | 162 bp |
| | b cat4R1 | 5'-TAGTGGGATGAGCAGCATCAA-3' | |
| | b cat4F2 | 5'-GCTGCTATGTTCCCTGAGACAT-3' | 260 bp |
| | b cat4R2 | 5'-TGAGCATTTACTTCAAAGCAGACT-3' | |
| 5 | b cat5F1 | 5'-AGGGGAGTAGTTTCAGAATGTCT-3' | 248 bp |
| | b cat5R1 | 5'-GGGAAAGGTTATGCAAGGTC-3' | |
| | b cat5F2 | 5'-AGATGGTGTCTGCTATTGTACGT-3' | 227 bp |
| | b cat5R2 | 5'-GCCTCATCAGAAATATTGTGAGT-3' | |
| 6 | b cat6F | 5'-ACTCACAATATTTCTGATGAGGC-3' | 289 bp |
| | b cat6R | 5'-AGGTGTCCAATGCTCCATG-3' | |
| 7 | b cat7F | 5'-AAAATAGGTTGGTAATATGGCTC-3' | 271 bp |
| | b cat7R | 5'-TGCAGATGCTATACACAAGACTC-3' | |
| 8 | b cat8F | 5'-AGGATTGATAGGCACTTCTAGCT-3' | 219 bp |
| | b cat8R | 5'-CAAGCACATACTCATCTTGACTCT-3' | |
| 9 | b cat9F1 | 5'-AGAGTCAAGATGAGTATGTGCTTG-3' | 218 bp |
| | b cat9R1 | 5'-CAGTACGCACAAGAGCCTCTA-3' | |
| | b cat9F2 | 5'-ATAAGAACAAGATGATGGTCTGC-3' | 270 bp |
| | b cat9R2 | 5'-CAATTCTGCAACAAAGGTAAATT-3' | |
| 10 | b cat10F | 5'-GATTTTGTTGAGTTGTATGCCA-3' | 240 bp |
| | b cat10R | 5'-TTTTAGATAGCCAGGTATCACTG-3' | |
| 11 | b cat11F | 5'-TACGGGGAACTTCGGGTA-3' | 263 bp |
| | b cat11R | 5'-TGGACATAAAACCTAGAACACTTC-3' | |
| 12 | b cat12F | 5'-GGCTTGCCATGTTTTAGCTT-3' | 243 bp |
| | b cat12R | 5'-ACATCTGCTAAAGGCTTTGGT-3' | |
| 13 | b cat13F | 5'-AAGTCTCAGTTTTTCCTCAAGG-3' | 197 bp |
| | b cat13R | 5'-CCAGATAAATAACTGCTCACATT-3' | |
| 14 | b cat14F | 5'-CCTTGCTTTGTGCATGTTTA-3' | 122 bp |
| | b cat14R | 5'-TGATCTGGAGTTAATCGAGAAA-3' | |
| 15 | b cat15F | 5'-TTTTGTTGACACCCTGACTCTT-3' | 286 bp |
| | b cat15R | 5'-AAAGTATTTACCCAAACTGGC-3' | |

TABLE 4

Primers used for the amplification of TP53. Part of exon 4 and all of exons 5-9 were amplified using the primers designed by Dahiya et al. 1996 (Br. J. Cancer 74, 264-268).

| Exon | Primer name | Sequence | Product size | Annealing Temp. |
|---|---|---|---|---|
| 2 | P53_2F | 5'-CCTCTTGCAGCAGCCAGACT-3' | 215 bp | 57° C. |
|  | P53_2R | 5'-AGCAGAAAGTCAGTCCCATGAAT-3' |  |  |
| 3 | P53_3F | 5'-AGCGAAAATTCATGGGACTGA-3' | 204 bp | 50° C. |
|  | P53_3R | 5'-TCCGGGGACAGCATCAAAT-3' |  |  |
| 4 | P53_4F1 | 5'-CTCTTTTCACCCATCTACAGTCC-3' | 225 bp | 57° C. |
|  | P53_4F1 | 5'-TCTGGGAAGGGACAGAAGAT-3' |  |  |
| 10 | P53_10F | 5'-GTTGCTTTTGATCCGTCATAAA-3' | 233 bp | 54° C. |
|  | P53_10R | 5'-AGGAAGGGGCTGAGGTCAC-3' |  |  |
| 11 | P53_11F | 5'-ACCCTCTCACTCATGTGATGTCA-3' | 250 bp | 50° C. |
|  | P53_11R | 5'-GTGCTTCTGACGCACACCTATT-3' |  |  |

TABLE 5

Primers used for the amplification of hMYH

| Exon | Primer name | Sequence | Product size | Annealing Temp. |
|---|---|---|---|---|
| 1 | Y1F | 5'-GAAGCTGCGGGAGCTGAAA-3' | 133 bp | 60° C. |
|  | Y1R | 5'-ATCCCCGACTGCCTGAACC-3' |  |  |
| 2 | Y2F | 5'-CTGCATTTGGCTGGGTCTTT-3' | 263 bp | 54° C. |
|  | Y2R | 5'-CGCACCTGGCCCTTAGTAAG-3' |  |  |
| 3 | Y3F | 5'-AGCCTGTGCAGGGATGATTG-3' | 272 bp | 57° C. |
|  | Y3R | 5'-CAACCCCAGATGAGGAGTTAGG-3' |  |  |
| 4 | Y4F | 5'-CTCATCTGGGGTTGCATTGA-3' | 167 bp | 57° C. |
|  | Y4R | 5'-GGGTTGGCATGAGGACACTG-3' |  |  |
| 5 | Y5F | 5'-GGGCAGGTCAGCAGTGTC-3' | 189 bp | 57° C. |
|  | Y5R | 5'-TACACCCACCCCAAAGTAGA-3' |  |  |
| 6 | Y6F | 5'-TACTTTGGGGTGGGTGTAGA-3' | 185 bp | 54° C. |
|  | Y6R | 5'-AAGAGATCACCCGTCAGTCC-3' |  |  |
| 7 | Y7F | 5'-GGGACTGACGGGTGATCTCT-3' | 186 bp | 54° C. |
|  | Y7R | 5'-TTGGAGTGCAAGACTCAAGATT-3' |  |  |
| 8 | Y8F | 5'-CCAGGAGTCTTGGGTGTCTT-3' | 240 bp | 57° C. |
|  | Y8R | 5'-AGAGGGGCCAAAGAGTTAGC-3' |  |  |
| 9 | Y9F | 5'-AACTCTTTGGCCCCTCTGTG-3' | 196 bp | 57° C. |
|  | Y9R | 5'-GAAGGGAACACTGCTGTGAAG-3' |  |  |
| 10 | Y10F | 5'-GTGCTTCAGGGGTGTCTGC-3' | 262 bp | 57° C. |
|  | Y10R | 5'-TGTCATAGGGCAGAGTCACTCC-3' |  |  |
| 11 | Y11F | 5'-TAAGGAGTGACTCTGCCCTATG-3' | 248 bp | 54° C. |
|  | Y11R | 5'-GCCAAGAGGGGCTTTAGG-3' |  |  |
| 12 | Y12F | 5'-AGCCCCTCTTGGCTTGAGTA-3' | 298 bp | 57° C. |
|  | Y12R | 5'-TGCCGATTCCCTCCATTCT-3' |  |  |
| 13 | Y13F | 5'-AGGGCAGTGGCATGAGTAAC-3' | 242 bp | 57° C. |
|  | Y13R | 5'-GGCTATTCCGCTGCTCACTT-3' |  |  |
| 14 | Y14F | 5'-TTGGCTTTTGAGGCTATATCC-3' | 256 bp | 54° C. |
|  | Y14R | 5'-CATGTAGGAAACACAAGGAAGTA-3' |  |  |
| 15 | Y15F | 5'-TGAAGTTAAGGGCAGAACACC-3' | 205 bp | 54° C. |
|  | Y15R | 5'-GTTCACCCAGACATTCGTTAGT-3' |  |  |
| 16 | Y16F | 5'-AGGACAAGGAGAGGATTCTCTG-3' | 224 bp | 54° C. |
|  | Y16R | 5'-GGAATGGGGGCTTTCAGA-3' |  |  |

TABLE 6

Primers used for the amplification of hOGG1

| Exon | Primer name | Sequence | Product size | Annealing Temp. |
|---|---|---|---|---|
| 1 | M1F | 5'-CTTTGGGCGTCGACGAG-3' | 237 bp | 57° C. |
|  | M1R | 5'-GAGGGGACAGGCTTCTCAG-3' |  |  |
| 2 | M2F1 | 5'-ATTGAGTGCCAGGGTTTGTCA-3' | 245 bp | 57° C. |
|  | M2R1 | 5'-CGGAACCCCAGTGGTGATAC-3' |  |  |
|  | M2F2 | 5'-TGTACTAGCGGGATCAAGTAT-3' | 286 bp | 50° C. |
|  | M2R2 | 5'-TGGCAAAACTGAGTCATAG-3' |  |  |
| 3 | M3F1 | 5'-GTCTGGTGTTGCTTTCTCTAAC-3' | 229 bp | 50° C. |
|  | M3R1 | 5'-GTGATGCGGGCGATGTT-3' |  |  |
|  | M3F2 | 5'-TCTCCAGGTGTGCGACTGC-3' | 275 bp | 57° C. |
|  | M3R2 | 5'-AGGAAGCCTTGAGAAGGTAACC-3' |  |  |

TABLE 6-continued

Primers used for the amplification of hOGG1

| Exon | Primer name | Sequence | Product size | Annealing Temp. |
|---|---|---|---|---|
| 4 | M4F | 5'-GGAAGAACTTGAAGATGCCT-3' | 296 bp | 55° C. |
|   | M4R | 5'-GCTCATTTCCTGCTCTCC-3' | | |
| 5 | M5F | 5'-CCGGCTTTGGGGCTATA-3' | 279 bp | 57° C. |
|   | M5R | 5'-GTTTCTACCATCCCAGCCCA-3' | | |
| 6 | M6F | 5'-TACTTCTGTTGATGGGTCAC-3' | 153 bp | 55° C. |
|   | M6R | 5'-TGGAGGAGAGGAAACCTAG-3' | | |
| 7 | M7F | 5'-ACCTCCCAACACTGTCACTA-3' | 265 bp | 55° C. |
|   | M7R | 5'-CCCTCCCCAACATGAGA-3' | | |
| 8 | M8F1 | 5'-CTGTGGCCCACGCACTTGTG-3' | 253 bp | 57° C. |
|   | M8R1 | 5'-ACGTCCTTGGTCCAGCAGTGGT-3' | | |
|   | M8F2 | 5'-GAGAGGGGATTCACAAGGTG-3' | 287 bp | 55° C. |
|   | M8R2 | 5'-GCCATTAGCTCCAGGCTTAC-3' | | |

TABLE 7

Primers used for the amplification of hMTH

| Exon | Primer Name | Sequence | Product size | Annealing Temp. |
|---|---|---|---|---|
| 2 | T2F | 5'-GCAAGGACAGAGGGCTTTCTG-3' | 249 bp | 67° C. |
|   | T2R | 5'-CCAGCAGGCCATCAACTGAT-3' | | |
| 3 | T3F | 5'-GCACGTCATGGCTGACTCT-3' | 246 bp | 57° C. |
|   | T3R | 5'-CTGGGAAAGCCGGTTCTAT-3' | | |
| 4 | T4F | 5'-TCCCTGGGCTGTGTGTAGAT-3' | 298 bp | 57° C. |
|   | T4R | 5'-GAGATGGGACCCGCATAGT-3' | | |
| 5 | T5F | 5'-TGAAGTTTGGGTTGCACCTC-3' | 281 bp | 57° C. |
|   | T5R | 5'-AGATGGTTTGCGGCTGTTC-3' | | |

TABLE 8

LD-PCR primers used for the amplification of exon 15 of APC for DNA extracted from fresh tissue. Primer nucleotide numbers in parentheses are cited according to Accession No. NM_000038.

| Primer name | Sequence | Product Size |
|---|---|---|
| N15F (1997) | 5'-GCAAATCCTAAGAGAGAACAACTGT-3' | 6.67 kb |
| N15R1 (8684) | 5'-TCCAGAACAAAAACCCTCTAACAAG-3' | |
| N15F (1997) | 5'-GCAAATCCTAAGAGAGAACAACTGT-3' | 3.59 kb |
| NS15 4R (5571) | 5'-CCTTCAATAGGCGTGTAATG-3' | |
| NS15 3F (3649) | 5'-AAAGCAGTAAAACCGAACAT-3' | 5.07 kb |
| N15R (8698) | 5'-TCAAATATGGCTrCCAGAACAAA-3' | |

TABLE 9

LD-PCR primers used for the amplification of exons 10 to 16 of hMYH.

| Primer name | Sequence | Product Size |
|---|---|---|
| Y10F1L | 5'-GCTGATCCCAGCAGCACCCTTGTTT-3' | 3.1 kb |
| Y16RL | 5'-AATGGGGGCTTTCAGAGGTGTCACT-3' | |

TABLE 10

Primers used for RT-PCR analysis.

| Region amplified | Primer name | Sequence |
|---|---|---|
| Exons 3-12 of APC | APCFEx3 | 5'-GAGGGTTTGTAAATGGAAGCAG-3' |
|  | APCjREx11-12 | 5'-CTCATGCAGCCTTTCATAGAGC-3' |
| Exons 12-14 of hMYH | rY12F | 5'-GTGGTCAACTTCCCCAGAAA-3' |
|  | rY14R | 5'-GGCCAGCCCATATACTTGAT-3' |

TABLE 11

Bi-directional sequencing reactions for automated sequencing of RT-PCR product clones spanning exons 1-14 of APC.

| Reaction | Primer name | Sequence |
|---|---|---|
| 1 | NS1_14F (39) | 5'-ATGGCTGCAGCTTCATATGA-3' |
|  | NS1_14R2 (1049) | 5'-GCTGTCTTGGGAGCTAGAC-3' |
| 2 | NS1_14F2 (892) | 5'-ACCATGAAACAGCCAGTGT-3' |
|  | NS1_14R (1978) | 5'-CTGTGGTCCTCATTTGTAG-3' |

TABLE 12

Bi-directional sequencing reactions for automated sequencing of LD-PCR products and clones spanning exon 15 of APC.

| Reaction | Primer name | Sequence |
|---|---|---|
| 1 | NS15 1F (1997) | 5'-GCAAATCCTAAGAGAGAACA-3' |
|   | NS15 8R (3146) | 5'-GACTTTGCCTTCCAGAGTTC-3' |
| 2 | NS15 2F (2810) | 5'-AAGCTCTGCTGCCCATACAGA-3' |
|   | NS15 7R (3935) | 5'-CTGCTATTTGCAGGGTATTA-3' |
| 3 | NS15 3F (3649) | 5'-AAAGCAGTAAAACCGAACAT-3' |
|   | NS15 3R (4775) | 5'-TTGTTGGCATGGCAGAAATA-3' |
| 4 | NS15 4F (4480) | 5'-TTCTTCCAGATGCTGATACT-3' |
|   | NS15 4R (5571) | 5'-CCTTCAATAGGCGTGTAATG-3' |
| 5 | NS15 5F (5234) | 5'-GCCCAAAGGGAAAAGTCACA-3' |
|   | NS15 5R (6346) | 5'-ATTTTGCACCTTCCTGAATAG-3' |
| 6 | NS1S 6F (6015) | 5'-CCTGACTCACAGGGAGAAC-3' |
|   | NS15 6R (7135) | 5'-CTGTCTACCTGGAGATGTAT-3' |
| 7 | NS15 7F (6807) | 5'-GCCTCCAAAAGCCCTAGTGA-3' |
|   | NS15 2R (7920) | 5'-AGCACCTGAGGAAACGGTCTG-3' |
| 8 | NS15 8F (7552) | 5'-GAAAACTCCCACCTAATCTC-3' |
|   | NS15 1R (8684) | 5'-AACAAAAACCCTCTAACAAG-3' |

TABLE 13

Primers used to assay for E1317Q

| Primer name | Sequence |
|---|---|
| E1317QLF (3652) | 5'-GCAGTAAAACCGAACATATG-3' |
| E1317QR (4137) | 5'-TGGACTTTTGGGTGTCTG-3' |
| E1317QSF (3934) | 5'-CTAATACCCTGCAAATAGCA-3' |
| E1317QR (4137) | 5'-TGGACTTTTGGGTGTCTG-3' |

TABLE 14

Assays for missense variants in hMYH. All ARMS reactions incorporated internal control primers (AJ31 and AJ32, Jones et al. 2000) to validate the assay.

| Variant | Exon | Assay |
|---|---|---|
| V22M (66 G→A) | 2 | NcoI digest |
| Y165C (494 A→G) | 7 | Normal ARMS (165N 5'-CGCCGGCCACGAGAATGGT-3') |
|  |  | Mutant ARMS (165M 5'-CGCCGGCCACGAGAATTTGC-3') |
|  |  | Common (165C 5'-AGTGCTTTCCCTGGAGGTGAGA-3') |
| R260Q (779 G→A) | 10 | Normal ARMS (260N 5'-CTTGGTTGAAATCTCCTGCCC-3') |
|  |  | Mutant ARMS (260M 5'-CTTGGTTGAAATCTCCTGACT-3') |
|  |  | Common (260C 5'-CGAGCCATTGGTGCTGATC-3') |
| H324Q (972 C→G) | 12 | Normal ARMS (324N 5'-CCAGCTCCCAACACTGGAGAC-3') |
|  |  | Mutant ARMS (324M 5'-CCAGCTCCCAACACTGGAGAG-3') |
|  |  | Common (324C 5'-CCCAGGCTGTTCCAGAACAC-3') |
| G382D (1145 G→A) | 13 | BglII digest |
| S501F (1502 C→T) | 16 | Normal ARMS (501N 5'-GCTTTTTCCGACTGCACGCAG-3') |
|  |  | Mutant ARMS (501M 5'-GCTTTTTCCGACTGCACGAAA-3') |
|  |  | Common (501C 5'-GCATTCCAGGCTAAGCCTAGC-3') |

TABLE 15

Primers used for site directed mutagenesis of mutY

| Mutation | Primer name | Sequence |
|---|---|---|
| Y82C | Y82C_F | 5'-GCGCGCGCGGGCGCAATAGCCAAGCCC-3' |
| G253D | G253D_F | 5'-CCGCCCCACAAGTCGCTCGGCGGACGC-3' |

The invention claimed is:

1. An isolated nucleic acid having 19 or more contiguous nucleotides, including position 494, of SEQ ID NO:130, or the complement thereof.

2. The isolated nucleic acid or the complement thereof of claim 1, wherein said nucleic acid has the sequence of SEQ ID NO:130, or the complement thereof.

3. An isolated nucleic acid or the complement thereof, wherein said isolated nucleic acid has 10-20 or more contiguous nucleotides, including position 494, of SEQ ID NO:130.

4. An isolated nucleic acid or the complement thereof, wherein said isolated nucleic acid has 20 or more contiguous nucleotides, including position 494, of SEQ ID NO:130.

5. The isolated nucleic acid or complement thereof of claim 1, wherein said isolated nucleic acid has 20-25 or more contiguous nucleotides, including position 494, of SEQ ID NO:130, or the complement thereof.

6. The isolated nucleic acid or complement thereof of claim 1, wherein said isolated nuefeic acid has 25 or more contiguous nucleotides, including position 494, of SEQ ID NO:130, or the complement thereof.

7. The isolated nucleic acid or complement thereof of claim 1, wherein said isolated nucleic acid has 26 or more contiguous nucleotides, including position 494, of SEQ ID NO:130, or the complement thereof.

8. The isolated nucleic acid or complement thereof of claim 1, wherein said isolated nucleic acid has 186 or more contiguous nucleotides, including position 494, of SEQ ID NO:130.

9. A micro-array comprising the nucleic acid or complement thereof of claim 1.

* * * * *